United States Patent
McCauley et al.

(10) Patent No.: US 6,316,474 B1
(45) Date of Patent: Nov. 13, 2001

(54) 2-BENZYL AND 2-HETEROARYL BENZIMIDAZOLE NMDA/NR2B ANTAGONISTS

(75) Inventors: John A. McCauley, Maple Glen, PA (US); Cory R. Theberge, Portsmouth, NH (US); Nigel J. Liverton, Harleysville, PA (US); David A. Claremon, Maple Glen, PA (US); Christopher F. Claiborne, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/696,501

(22) Filed: Oct. 25, 2000

Related U.S. Application Data

(60) Provisional application No. 60/162,351, filed on Oct. 29, 1999.

(51) Int. Cl.$^7$ .......................... A01N 43/40; A01N 43/52; C07D 401/12; C07D 235/04
(52) U.S. Cl. .......................... 514/338; 514/394; 514/395; 546/273.4; 548/304.7; 548/305.1; 548/306.4; 548/307.4; 548/310.1; 548/243
(58) Field of Search ............................... 548/304.7, 309.7, 548/305.1, 306.1; 546/273.4; 514/338, 394, 395

(56) References Cited

U.S. PATENT DOCUMENTS

| | | |
|---|---|---|
| 4,213,994 | 7/1980 | Gebert et al. . |
| 4,695,575 | 9/1987 | Janssens et al. . |
| 4,820,757 | 4/1989 | Spang et al. . |
| 5,306,723 | 4/1994 | Chenard . |
| 5,314,880 * | 5/1994 | Whittaker et al. ............. 514/80 |
| 5,385,925 * | 1/1995 | Narr et al. ................. 514/382 |
| 5,436,255 | 7/1995 | Butler . |
| 5,459,147 * | 10/1995 | Hauel et al. ................ 514/303 |
| 5,714,498 | 2/1998 | Kulagowski et al. . |
| 5,807,874 * | 9/1998 | LaVoie et al. ............... 514/338 |
| 5,817,756 | 10/1998 | Kyle et al. . |
| 5,889,019 | 3/1999 | Mitch . |

FOREIGN PATENT DOCUMENTS

| | | |
|---|---|---|
| 0 441 506 B1 | 7/1994 | (EP) . |
| 0 787 493 A1 | 8/1997 | (EP) . |
| WO 91/17156 | 11/1991 | (WO) . |
| WO 92/19502 | 11/1992 | (WO) . |
| WO 93/02052 | 2/1993 | (WO) . |
| WO 94/29571 | 12/1994 | (WO) . |
| WO 95/28057 | 10/1995 | (WO) . |
| WO 96/37226 | 11/1996 | (WO) . |

OTHER PUBLICATIONS

J. D. Kristensen, et al., Pain, 51:249–253(1992).
K. Eida, et al., Pain,61:221–228(1995).
D. J. Knox, et al., Anaesth. Intensive Care, 23:620–622(1995).
M. B. Max et al., Clin Neuropharmacol., 18:360–368(1995).
I. Ishii, et al., J. Biol. Chem.,268:2836–2843(1993).
A. Wenzel, et al., Neuro Report, 7:45–48(1995).
D. J. Laurie, et al., Mol. Brain Res., 51:23–32(1997).
S. Boyce, et al., Neuropharmacology, 38:611–623(1999).
Z.–L. Zhou et al., J. Med. Chem., 42:2993–3000(1999).
T.F. Gregory et al., Poster#94, 218th Nat'l Meeting Am. Chem. Soc., New Orleans, Louisiana, Aug. 22–26, 1999.
J.N.C. Kew, et al., Brit. J. Pharmacol., 123;463(1998).

* cited by examiner

*Primary Examiner*—Floyd D. Higel
*Assistant Examiner*—Kamal Saeed
(74) *Attorney, Agent, or Firm*—Shu Muk Lee; David L. Rose

(57) ABSTRACT

Benzimidazoles, substituted in the 2-position by substituted benzyl groups or heteroaryl groups are effective as NMDA NR2B antagonists and are useful for relieving pain.

13 Claims, No Drawings

2-BENZYL AND 2-HETEROARYL BENZIMIDAZOLE NMDA/NR2B ANTAGONISTS

This application claims priority from U.S. Provisional application Ser. No. 60/162,351 filed Oct. 29, 1999.

BACKGROUND OF THE INVENTION

FIELD OF THE INVENTION

This invention relates to novel benzimidazole derivatives. In particular, this invention relates to novel benzimidazoles, substituted in the 2-position by substituted benzyl groups or heteroaryl groups, that are effective as NMDA NR2B antagonists useful for relieving pain.

Ions such as glutamate play a key role in processes related to chronic pain and pain-associated neurotoxicity—primarily by acting through N-methyl-D-aspartate ("NMDA") receptors. Thus, inhibition of such action—by employing ion channel antagonists, particularly NMDA antagonists—can be beneficial in the treatment and control of pain.

Known NMDA antagonists include ketamine, dextromophan, and 3-(2-carboxypiperazin-4-yl)-propyl-1-phosphonic acid ("CPP"). Although these compounds have been reported to produce symptomatic relief in a number of neuropathies including postherpetic neuralgia, central pain from spinal cord injury, and phantom limb pain, (J. D. Kristensen, et al., *Pain*, 51:249–253 (1992); K. Eide, et al., *Pain*, 61:221–228 (1995); D. J. Knox, et al., *Anaesth. Intensive Care* 23:620–622 (1995); and M. B. Max, et al., *Clin. Neurophartnacol.* 18:360–368 (1995)) widespread use of these compounds is precluded by their undesirable side effects. Such side effects at analgesic doses include psychotomimetic effects such as dizziness, headache, hallucinations, dysphoria, and disturbances of cognitive and motor function. Additionally, more severe hallucinations, sedation, and ataxia are produced at doses only marginally higher than analgesic doses. Thus, it would be desirable to provide novel NMDA antagonists that are absent of undesirable side effects or that produce fewer and/or milder side effects.

NMDA receptors are heteromeric assemblies of subunits, of which two major subunit families designated NR1 and NR2 have been cloned. Without being bound by theory, it is generally believed that the various functional NMDA receptors in the mammalian central nervous system ("CNS") are only formed by combinations of NR1 and NR2 subunits, which respectively express glycine and glutamate recognition sites. The NR2 subunit family is in turn divided into four individual subunit types: NR2A, NR2B, NR2C, and NR2D. I. Ishii, et al.,*J. Biol. Chem.,* 268:2836–2843 (1993), A. Wenel, et al., *NeuralReport,* 7:45–48 (1995), and D. J. Laurie et al., *Mol. Brain Res.,* 51:23–32 (1997) describe how the various resulting combinations produce a variety of NMDA receptors differing in physiological and pharmacological properties such as ion gating properties, magnesium sensitivity, pharmacological profile, as well as in anatomical distribution.

For example, while NR1 is found throughout the brain, NR2 subunits are differentially distributed. In particular, it is believed that the distirbution map for NR2B lowers the probability of side effects while producing pain relief. For example, S. Boyce, et al., *Neuropharmacology,* 38:611–623 (1999) describes the effect of selective NMDA NR2B antagonists on pain with reduced side-effects. Thus, it would be desirable to provide novel NMDA antagonists that target the NR2B receptor.

U.S. Pat. No. 5,714,498 (International Patent Publication WO94/21615) describes benzimidazole-piperidine compounds utilized as dopamine D4 antagonists. Phenol compounds described as NMDA antagonists are described in U.S. Pat. Nos. 5,306,723 and 5,436,255, and in International Patent Publications WO91/17156, WO92/19502, WO93/02052, WO94/2957 1, WO95/28057, WO96/37226, and EP 04422506. Benzyl piperidines substituted with phenols or imidazoles are described in Z.-L. Zhou, et al., *J. Medicinal Chemistry,* 42:2993–3000(1999); T. F. Gregory, et al., Poster #94, 218th National Meeting American Chemical Society, New Orleans, La., Aug. 22–26, 1999. Other NMDA NR2B selective compounds are described in European Patent Publication EP 787493 and *British J. Pharmacol.,* 123:463 (1998). However, there continues to be a need for novel NMDA antagonists that target the NR2B receptor.

SUMMARY OF THE INVENTION

The present invention relates to benzimidazoles substituted in the 2-position with substituted benzyl groups. The present invention also forms novel pharmaceutical compositions utilizing these novel compounds. Further, this invention includes novel methods to treat pain by utilizing the novel compounds.

DETAILED DESCRIPTION OF THE INVENTION

In one aspect, the compounds of this invention are represented by Formula (I):

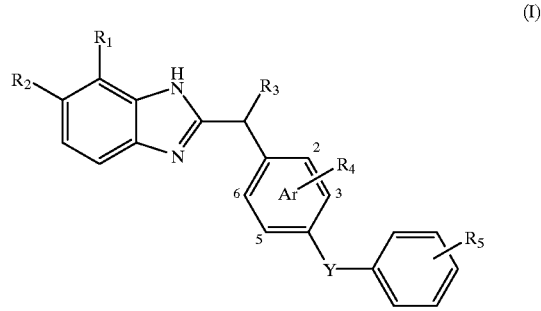

(I)

or pharmaceutically acceptable salts thereof, wherein $R_1$, $R_2$, $R_4$, and $R_5$ are independently H, chloro, fluoro, hydroxy, methoxy, trifluoromethyl, trifluoromethoxy, amino, cyano, nitro, $C_{1-7}$alkyl, aryl, amino$C_{1-4}$alkyl, $C_{1-4}$alkyl-carbonylamino, oxo-hydroxy-dibenzopyranyl-carboxyphenyl-thioueido, $R_6SO_2NH$—, $R_6SO_2N(CH_3)$—, $R_6SO_2NHCH_2$—, or oxo-hydroxy-dibenzopyranyl-carboxyphenyl-substituted carbonylamino-$C_{1-4}$alkyl-carbonylamino;

$R_3$ is H, OH, $NH_2$, alkylamine, arylamine, or a carbonyl oxygen;

$R_6$ is $C_{1-6}$alkyl, $C_{1-6}$alkenyl, phenyl$C_{1-3}$alkenyl, phenyl, naphthyl, or heterocyclic group, optionally substituted with 1–6 substituents, each substituent independently being halogen, $C_{1-4}$alkyl, $C_{1-4}$alkoxy, halo$C_{1-4}$alkoxy, amino, $C_{1-4}$alkylamino, di$C_{1-4}$alkylamino, $C_{1-4}$alkylcarbonylamino, phthalimidyl, phenylsulfonyl, or oxo-hydroxy-dibenzopyranyl-carboxyphenyl-thioueido;

Y is O, NH, $(CH_2)_nCO(CH_2)_n$, $(CH_2)_nCHR_3(CH_2)_n$, n is independently 0, 1, 2, 3, 4, or 5; and the central ring Ar is substituted with 0–3 nitrogen heteroatoms at any of positions 2, 3, 5, or 6.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

Unless otherwise stated, the terms "carbonyl" and "carbonylamino" include short $C_1$–$C_2$ termini. The terms include, for example, —CO—, —CONH—, —CH$_2$CO—, —CH$_2$CONH—, —C$_2$H$_4$CO—, —C$_2$H$_4$CONH—, —COCH$_2$—, —CONHCH$_2$—, —COC$_2$H$_4$—, —CONHC$_2$H$_4$—, —CH$_2$COCH$_2$—, —CH$_2$CONHCH$_2$—, —CH$_2$COC$_2$H$_4$—, —CH$_2$CONHC$_2$H$_4$—, —C$_2$H$_4$COC$_2$H$_4$—, and —C$_2$H$_4$CONHC$_2$H$_4$—.

Unless otherwise stated, the term "$C_{1-4}$alkylamino" includes short $C_1$–$C_2$ termini. The term includes, for example, —CH$_2$NH—, —C$_2$H$_4$NH—, —C$_3$H$_6$NH—, —C$_4$H$_8$NH—, —CH$_2$NHCH$_2$—, —C$_2$H$_4$NHCH$_2$—, —C$_3$H$_6$NHCH$_2$—, —C$_4$H$_8$NHCH$_2$—, —CH$_2$NHC$_2$H$_4$—, —C$_2$H$_4$NHC$_2$H$_4$—, —C$_3$H$_6$NHC$_2$H$_4$—, and —C$_4$H$_8$NHC$_2$H$_4$—. Similarly, unless otherwise stated, the term "di$C_{1-4}$alkylamino" includes short $C_1$–$C_2$ termini.

The term "halogen" includes fluorine, chlorine, bromine and iodine atoms.

The term "aryl" includes, for example, phenyl and naphthyl.

Unless otherwise stated, the term "heterocyclic group" includes, for example, pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl, azetidinyl, pyrrolidinyl, piperidinyl, piperazinyl, morpholinyl, tetrahydrofuranyl, imidazolinyl, pyrolidin-2-one, piperidin-2-one, and thiomorpholinyl groups.

The central ring Ar in formula (I) is a six-membered aromatic ring that may be substituted with 0–3 nitrogen heteroatoms at any of positions 2, 3, 5, or 6. Accordingly, Ar can be for example phenyl, pyridinyl, pyridazinyl, pyrazinyl, pyrimidinyl, 2,3,5-triazinyl, or 2,3,6-triazinyl.

The term "optionally substituted" is intended to include both substituted and unsubstituted. Thus, for example, optionally substituted aryl could represent a pentafluorophenyl or a phenyl ring.

In one embodiment, the compounds of this invention are represented by Formula (I):

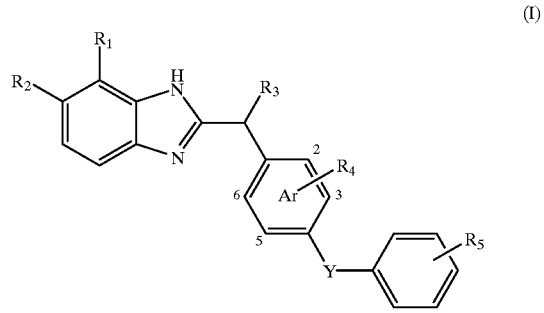

(I)

or pharmaceutically acceptable salts thereof, wherein $R_1$, $R_2$, $R_4$, and $R_5$ are independently H, chloro, fluoro, hydroxy, methoxy, trifluoromethyl, trifluoromethoxy, amino, cyano, nitro, $C_{1-7}$alkyl, aryl, amino$C_{1-4}$alkyl, $C_{1-4}$alkyl-carbonylamino, oxo-hydroxy-dibenzopyranyl-carboxyphenyl-thioueido, $R_6SO_2NH$—, $R_6SO_2N(CH_3)$—, $R_6SO_2NHCH_2$—, or oxo-hydroxy-dibenzopyranyl-carboxyphenyl-substituted carbonylamino-$C_{1-4}$alkyl-carbonylamino;

$R_3$ is H, OH, NH$_2$, alkyl amine, arylamine, or a carbonyl oxygen;

$R_6$ is $C_{1-6}$alkyl, $C_{1-6}$alkenyl, phenyl$C_{1-3}$alkenyl, phenyl, naphthyl, or heterocyclic group, optionally substituted with 1–6 substituents, each substituent independently being halogen, $C_{1-4}$alkyl, $C_{1-4}$alkoxy, halo$C_{1-4}$alkoxy, amino, $C_{1-4}$alkylamino, di$C_{1-4}$alkylamino, $C_{1-4}$alkylcarbonylamino, phthalimidyl, phenylsulfonyl, or oxo-hydroxy-dibenzopyranyl-carboxyphenyl-thioueido;

Y is O; and the central ring Ar is substituted with 0–3 nitrogen heteroatoms at any of positions 2, 3, 5, or 6.

In another embodiment, the compounds of this invention are represented by Formnula (I):

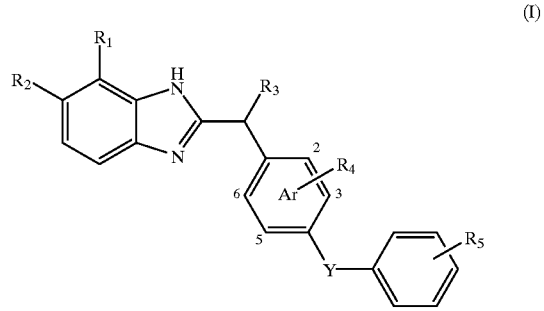

(I)

or pharmaceutically acceptable salts thereof, wherein $R_1$, $R_2$, and $R_4$ are independently H, chloro, fluoro, hydroxy, methoxy, trifluoromethyl, trifluoromethoxy, amino, cyano, nitro, $C_{1-7}$alkyl, aryl, amino$C_{1-4}$alkyl, $C_{1-4}$alkyl-carbonylamino, oxo-hydroxy-dibenzopyranyl-carboxyphenyl-thioueido, $R_6SO_2NH$—, $R_6SO_2N(CH_3)$—, $R_6SO_2NHCH_2$—, or oxo-hydroxy-dibenzopyranyl-carboxyphenyl-substituted carbonylamino-$C_{1-4}$alkyl-carbonylamino;

$R_5$ is H;

$R_3$ is H, OH, NH$_2$, alkyl amine, arylamine, or a carbonyl oxygen;

$R_6$ is $C_{1-6}$alkyl, $C_{1-6}$alkenyl, phenyl$C_{1-3}$alkenyl, phenyl, naphthyl, or heterocyclic group, optionally substituted with 1–6 substituents, each substituent independently being halogen, $C_{1-4}$alkyl, $C_{1-4}$alkoxy, halo$C_{1-4}$alkoxy, amino, $C_{1-4}$alkylamino, di$C_{1-4}$alkylamino, $C_{1-4}$alkylcarbonylamino, phthalimidyl, phenylsulfonyl, or oxo-hydroxy-dibenzopyranyl-carboxyphenyl-thioueido;

Y is O, NH, $(CH_2)_nCO(CH_2)_n$, $(CH_2)_nCHR_3(CH_2)_n$, n is independently 0, 1, 2, 3, 4, or 5; and the central ring Ar is substituted with 0–3 nitrogen heteroatoms at any of positions 2, 3, 5, or 6.

In yet another embodiment of this invention, the compounds of this invention are represented by Formula (I):

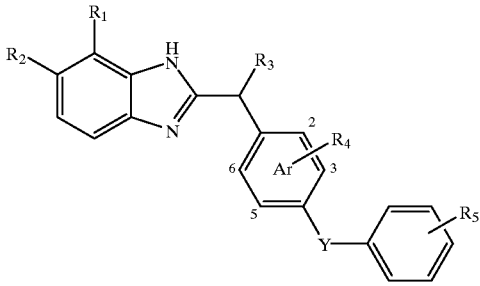

(I)

or pharmaceutically acceptable salts thereof, wherein $R_1$, $R_2$, and $R_4$ are independently H, chloro, fluoro, hydroxy, methoxy, trifluoromethyl, trifluoromethoxy, amino, cyano, nitro, $C_{1-7}$alkyl, aryl, amino$C_{1-4}$alkyl, $C_{1-4}$alkyl-carbonylamino, oxo-hydroxy-dibenzopyranyl-carboxyphenyl-thioueido, $R_6SO_2NH—$, $R_6SO_2N(CH_3)—$, $R_6SO_2NHCH_2—$, or oxo-hydroxy-dibenzopyranyl-carboxyphenyl-substituted carbonylamino-$C_{1-4}$alkyl-carbonylamino;

$R_5$ is H;

$R_3$ is H, OH, $NH_2$, alkyl amine, arylamine, or a carbonyl oxygen;

$R_6$ is $C_{1-6}$alkyl, $C_{1-6}$alkenyl, phenyl$C_{1-3}$alkenyl, phenyl, naphthyl, or heterocyclic group, optionally substituted with 1–6 substituents, each substituent independently being halogen, $C_{1-4}$alkyl, $C_{1-4}$alkoxy, halo$C_{1-4}$alkoxy, amino, $C_{1-4}$alkylamino, di$C_{1-4}$alkylamino, $C_{1-4}$alkylcarbonylamino, phthalimidyl, phenylsulfonyl, or oxo-hydroxy-dibenzopyranyl-carboxyphenyl-thioueido;

Y is O; and the central ring Ar is substituted with 0–3 nitrogen heteroatoms at any of positions 2, 3, 5, or 6.

Compounds described herein contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmacecutical compositions of this invention may include a pharmceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Experimental Protocols

Assessing the Activity of Selected Compounds to Inhibit NR1A/2B NMDA Receptor Activation (FLIPR Assay)

The activity of selected compounds to inhibit NR1A/2B NMDA receptor activation measured as NR1A/2B receptor-mediated $Ca^{2+}$ influx is assessed by the following procedure:

NR1A/2B receptor transfected L(tk) cells are plated in 96-well format at $3 \times 10^6$ cells per plate and grown for one-two days in normal growth media (Dulbeccos MEM with Na pyruvate, 4500 mgglucose, pen/strep, glutamine, 10% FCS and 0.5 mg/ml geneticin). NR1A/2B-expression in these cells is induced by the addition of 4 nM dexamethasone in the presence of 500 $\mu$M ketamine for 16–24 hours. After receptor induction cells are washed using a Labsystem Cellwasher two times with assay buffer (Hanks balanced salt solution (HBSS-$Mg^{++}$ free) containing 20 mM HEPES, 0.1% BSA, 2 mM $CaCl_2$ and 250 $\mu$M probenecid). The cells of each 96 well cell plate are loaded with the $Ca^{++}$ sensitive dye Fluo-3 (Molecular Probes, Inc.) at 4 $\mu$M in assay buffer containing 0.5% FBS, and 0.04% pluronic F-127 (Molecular Probes, Inc.) for 1 h at 37° C. avoiding light. The cells are then washed with the Cellwasher four times with assay buffer leaving them in 100 $\mu$l buffer. Test compounds in solution are pipetted by FLIPR (Fluorometric Imaging Plate Reader) into each test well for a 2 min pretreatment. During this time the fluorescence intensity is recorded (excitation at 488 nm and emission at 530 nm). The glutamate/glycine 50 μl agonist solution (final concentration 1 μM/1 μM) is then added by FLIPR into each well already containing 150 μl of buffer (containing the test compound or vehicle) and the fluorescence is continuously monitored for 10 min. The endpoint fluorescence values are used to determine an $IC_{50}$ value comparing the agonist-stimulated signal for the vehicle alone sample and that for the cells incubated with each concentration of test compound.

Determining the Apparent Dissociation Constant (Ki) of Compounds for Human $NR1A/NR_2B$ Receptors (Binding Assay)

The radioligand binding assay is performed at room temperature in 96-well microtiter plates with a final assay volume of 1.0 mL in 20 mM Hepes buffer (pH 7.4) containing 150 mM NaCl. Solutions of test compounds were prepared in DMSO and serially diluted with DMSO to yield 20 μL of each of 10 solutions differing by 3-fold in concentration. Non-specific binding (NSB) using hot AMD-1 (10 μM final concentration) and total binding (TB) by using DMSO (2% final concentration). A solution of NR1A/NR2B receptors (40 pM final concentration) and tritiated AMD-2 (1 nM final concentration) were added to the test compounds. After 3 h of incubation at room temperature, samples are filtered through Packard GF/B filters (presoaked in 0.05% PEI, polyethyleninine Sigma P-3143) and washed 10 times with 1 mL of cold 20 mM Hepes buffer per wash. After vacuum drying of the filter plates, 40 μL of Packard Microscint-20 was added and bound radioactivity determined in a Packard TopCount. The apparent dissociation constant (Ki), the maximum percentage inhibition ($\%I_{max}$), the minimum percentage inhibition ($\% I_{min}$) and the hill slope (nH) were determined by a non-linear least squares fitting the bound CPM data to Equation #1 below.

Equation #1:

$$CPM\ Bound = \frac{(SB)(\%\ I_{max} - \%\ I_{min})}{(1 + ([Drug]/(Ki[L-844,345]/K_D))^{nH})} + NSB + (SB)(1 - \%\ I_{max})$$

where, $K_D$ is the apparent dissociation constant for the radioligand for the receptor as determined by hot saturation and SB is the specifically bound CPM determined from the difference of TB and NSB.

AMD-1

AMD-2

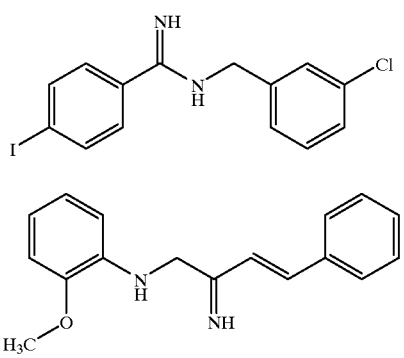

Compounds AMD-1 and AMD-2 can be synthesized in accordance with the following general reaction schemes.

SCHEME 1

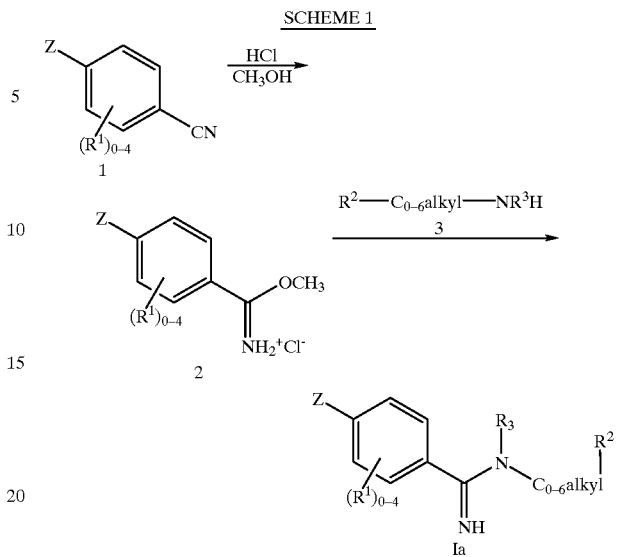

In accordance with scheme 1, hydrogen chloride is bubbled through a solution of the appropriately substituted benzonitrile 1 in methanol at room temperature. The volatiles are removed under reduced pressure and the resulting residue is triturated with ether and filtered to yield the desired imidate 2. Imidate 2 is dissolved in methanol at ambient temperature, treated with amine 3 at ambient temperature and stirred under argon. The volatiles are removed under reduced pressure and the residue purified by preparative HPLC or trituration with ether to afford amidine Ia.

SCHEME 2

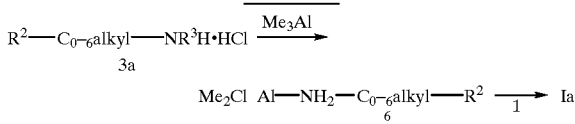

In accordance with scheme 2, at room temperature under argon, amine 3a is dissolved in ether and was treated with 1-M hydrogen chloride in ether (1 equiv.) in a single portion. The resulting precipitate is stirred vigorously for 10 minutes. The volatiles are removed under reduced pressure. The residue is suspended in toluene, cooled to 0° C. under argon, treated with 2.0-M trimethylaluminum (1.05 equiv.) in a dropwise manner, and stirred for 45 minutes at room temperature to afford intermediate 6 (not isolated). Compound 6 is added to a solution of nitrile 1 in toluene. The reaction is heated to 80° C. without stirring in a sealed tube for 18 h, cooled to ambient temperature, poured onto a silica gel column and eluted with methanol/dichloromethane to give the amidine 4.

Preparation of [$^{125}$I]AMD-1

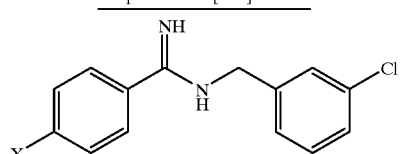

-continued

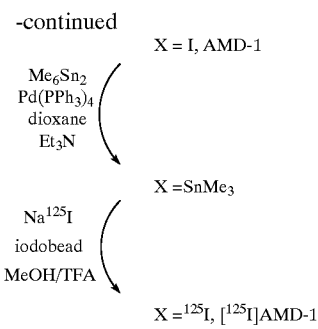

Tritiated AMD-1 was prepared by the following procedure: A mixture of AMD-1, hydrochloride salt, (5 mg, 0.012 mmol) in dioxane (0.2 mL) containing triethylamine (4 μL) was treated with hexamethylditin (5 μL), a catalytic amount of palladium catalyst and heated at 100° C. for 45 minutes. The reaction was cooled to room temperature, filtered through a glass wool plug, rinsed with methanol and concentrated in vacuo to give 10.7 mg of a brown oil. The oil was dissolved in methylene chloride and passed through a small silica column eluting with methylene chloride followed by 5% methanol/methylene chloride. Fractions containing the trimethylstannane (Rf 0.26 in 10% methanol/methylene chloride) were pooled and concentrated in vacuo to give 4.5 mg of the trimethylstannane as a clear colorless oil. This material was further purified by HPLC (C18 Econosil, 10×250 mm, 20 minute linear gradient, 30% MeCN:70% $H_2O$ (0.1% TFA) to 90% MeCN, 3 mL/min, 254 nm, retention time 15 minutes) to give 3mg of the trimethylstannane.

A $Na^{125}I$ shipping vial (10 mCi, Amersham) was charged with a stir bar, an iodobead, 50 μL of methanol and stirred five minutes at room temperature. A solution of the trimethylstannane (0.1 mg) in 50 μL of methanol containing 5 μL of trifluoroacetic acid was added and the reaction was stirred for five minutes. The reaction was quenched with 50 μL of ammonium hydroxide and purified by HPLC (C18 Vydac protein and peptide column, 4.6×250 mm, 20 minute linear gradient, 30% MeCN:70% $H_2O$ (0.1% TFA) to 90% MeCN, 1 mL/min, retention time 11 minutes). Fractions containing the radioactive product were pooled and concentrated in vacuo to give 989 μCi of [$^{125}I$]AMD-1 with a specific activity of 898 Ci/mmol as measured by UV absorbance at 272 nm.

Synthesis of Tritiated AMD-2

Tritiated AMD-2 was prepared by the following procedure: The phenol of AMD-2 (2 mg, 0.008 mmol) dissolved in dimethylformamide (0.6 mL) and potassium carbonate (1.2 mg) for 1 hr. High specific activity tritiated methyl iodide (50 mCi, 0.0006 mmol, in toluene 1 mL, American Radiolabeled Chemicals) was added at room temperature and stirred for 2 hours. The reaction mixture was filtered using a Whatman PTFE 0.45 μm syringeless filter device to remove any insoluable potassium carbonate, washed with Abs. ethanol (2 mL, Pharmco), and the combined filtrates were concentrated to dryness at room temperature using a rotary evaporator; this also removed any unreacted tritiated methyl iodide. The residue was purified by HPLC chromatography on a Phenomenx Luna C8 semi-prep column (Luna 5 micro C8(2), 250×10.0 mm) using a gradient system of 20/80 acetonitrile/water with 0.1% trifluoroacetic acid to 100% acetronitrile with 0.1% trifluoroacetic acid in 20 min. Total activity of the product was 8 mCi. Further purification was effected by absorption onto a Waters C-18 Sep-pak column (Waters Sep-Pak PLUS C18) and elution with water followed by absolute ethanol. The product was diluted with absolute ethanol (10 mL) before submission for final analysis.

The compounds of this invention exhibit less than 50 μM in the FLIBR and binding assays. Thus, the compounds and pharmaceutical compositions of this invention have been found to exhibit biological activity as NMDA NR2B antagonists. Accordingly, another aspect of the invention is the treatment of pain, migraine, depression, anxiety, schizophrenia, Parkinson's disease, or stroke—maladies that are amenable to amelioration through inhibition of NMDA NR2B receptors—by the administration of an effective amount of the compounds of this invention.

The following examples are provided to more fully illustrate the present invention, and are not to be construed as limiting the scope of the claims in any manner.

EXAMPLES

Scheme 1

Compounds of this invention can be prepared by the following general procedure, scheme 1:

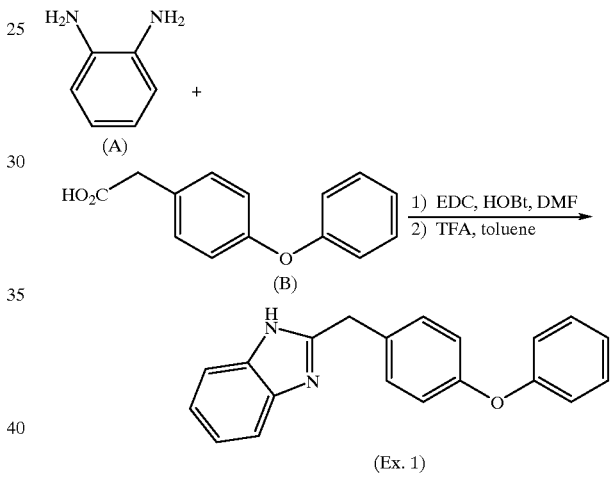

Example 1

2-(4-Phenoxy-benzyl)-1H-benzimidazole.

(Ex. 1)

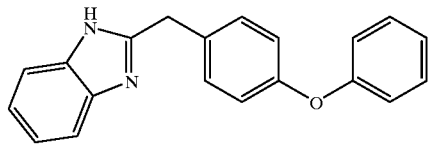

Example 1 was prepared by the following procedure. To a solution of (4-phenoxy-phenyl)-acetic acid (B) (500 mg, 2.19 mmol) in DMF (N,N-dimethylformamide) (5 mL) was added EDC (1,2-dichloroethane) (460 mg, 2.41 mmol), HOBt (327 mg, 2.41 mmol) and phenylenediamine (A) (236 mg, 2.19 mmol). The reaction mixture was stirred at room temperature for 1 h followed by quenching with aqueous $NaHCO_3$ and EtOAc. The layers were separated and the organic layer was washed twice with water, dried over $Na_2SO_4$, filtered, and concentrated.

The resulting crude product was dissolved in a mixture of trifluoroacetic acid/toluene (TFA/toluene) (1:1, 4 mL) and heated to 70° C. for 1 h. The mixture was then cooled, concentrated and partitioned between aqueous 1M NaOH and EtOAc. The organic layer was dried over Na$_2$SO$_4$, filtered, and concentrated. The resulting crude oil was purified by silica gel chromatography (gradient elution, 1:1 hexanes:EtOAc to EtOAc) to give Ex.1 (600 mg) as a white solid: $^1$H NMR (300 MHz, CD$_3$OD) δ7.75 (d, 1 H), 7.39–7.20 (m, 7 H), 7.15 (t, 1 H), 7.00 (m, 3 H), 4.16 (s, 2 H) ppm; mass spectrum m/z 301 [(M+H)$^+$; calcd for C$_{20}$H$_{17}$N$_2$O: 301].

Scheme 2

Compounds of this invention can be prepared by the following general procedure, scheme 2:

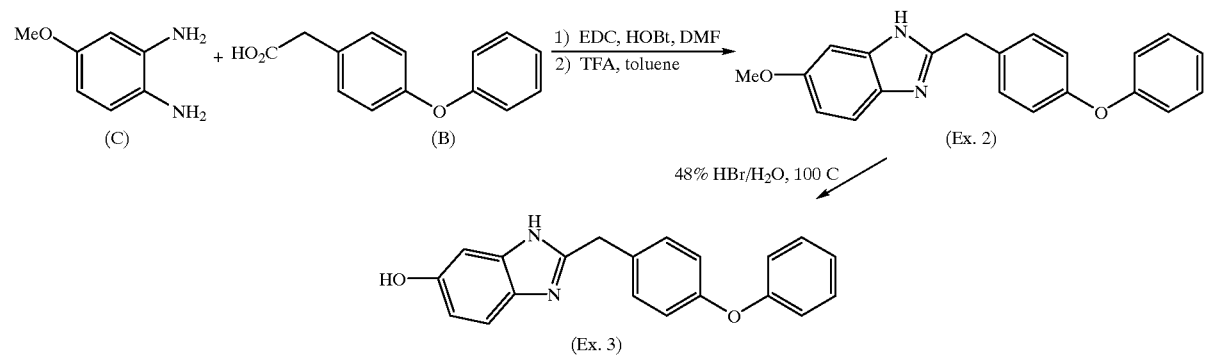

Example 2

6-Methoxy-2-(4-phenoxy-benzyl)-1H-benzimidazole.

(Ex. 2)

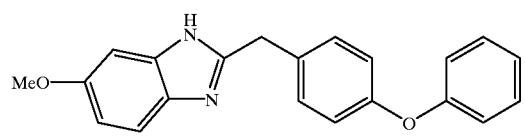

Example 2 was prepared by the following procedure. To a solution of (4-phenoxy-phenyl)-acetic acid (B) (500 mg, 2.19 mmol) in DMF (5 mL) was added EDC (460 mg, 2.41 mmol), HOBt (327 mg, 2.41 mmol) and 4-methoxy phenylenediamine (A) (302 mg, 2.19 mmol). The reaction mixture was stirred at room temperature for 1 h followed by quenching with aqueous NaHCO$_3$ and EtOAc. The layers were separated and the organic layer was washed twice with water, dried over Na$_2$SO$_4$, filtered, and concentrated.

The resulting crude product was dissolved in a mixture of TFA/toluene (1:1, 4 mL) and heated to 70° C. for 1 h. The reaction mixture was cooled, concentrated and partitioned between aqueous 1M NaOH and EtOAc. The organic layer was dried over Na$_2$SO$_4$, filtered, and concentrated. The resulting crude oil was purified by silica gel chromatography (gradient elution, 1:1 hexanes:EtOAc to EtOAc) to yield Ex. 2 (600 mg) as a white solid: $^1$H NMR (300 MHz, CD$_3$OD) δ7.60 (d, 1 H), 7.39 m, 4, H), 7.17 (m, 3 H), 7.00 (m, 4 H), 4.49 (s, 2 H), 3.89 (s, 3 H) ppm; mass spectrum m/z 331 [(M+H)$^+$; calcd for C$_{21}$H$_{19}$N$_2$O$_2$: 331].

Example 3

2-(4-Phenoxy-benzyl)-3H-benzimidazol-5-ol (Ex. 3)

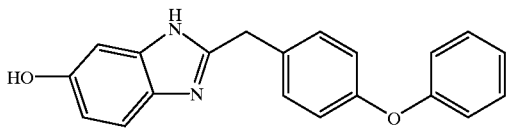

Example 3 was prepared by the following procedure. A solution of Ex. 2 (100 mg, 0.30 mmol) in HBr/H$_2$O (48%, 2 mL) was heated to 100° C. for 15 h. The reaction mixture was cooled and concentrated. The product was purified by preparative reverse-phase HPLC, to give the TFA salt of Ex. 3. The free base was prepared by dissolving in EtOAc and saturated aqueous NaHCO$_3$, separating the layers, drying the organic layer over Na$_2$SO$_4$, filtering, and concentrating to yield Ex. 3 as a white solid (90 mg): $^1$H NMR (300 MHz, DMSO-d$_6$) δ8.99 (s, 1 H), 7.38 (m, 5 H), 7.22 (d, 1 H), 7.09 (t, 1 H), 6.95 (m, 3 H), 6.77 (s, 1 H), 6.59 (dd, 1 H, 4.05 (s, 2 H) ppm; mass spectrum m/z 317 [(M+H)$^+$; calcd for C$_{20}$H$_{17}$N$_2$O$_2$: 317].

Scheme 3

Compounds of this invention can be prepared by the following general procedure, scheme 3:

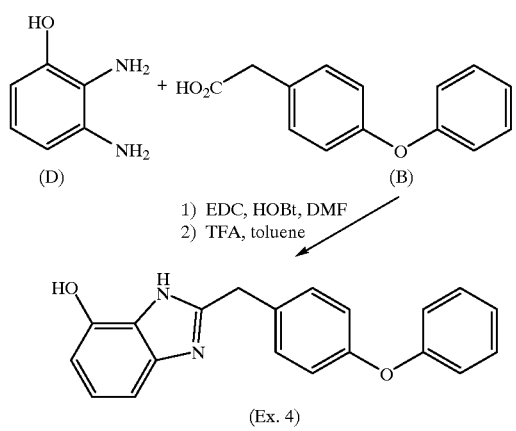

Example 4

2-(4-Phenoxy-benzyl)-3H-benzimidazol-4-ol

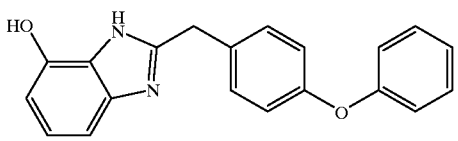
(Ex. 4)

Example 4 was prepared by the following procedure. To a solution of (4-phenoxy-phenyl)-acetic acid (B) (45 mg, 0.2 mmol) in DMF (500 µL) was added EDC (38 mg, 0.2 mmol), HOBt (27 mg, 0.2 mmol) and 2,3-diaminophenol (D) (25 mg, 0.2 mmol). The resulting reaction mixture was stirred at room temperature for 1 h followed by quenching with aqueous $NaHCO_3$ and EtOAc. The layers were separated and the organic layer was washed twice with water, dried over $Na_2SO_4$, filtered, and concentrated.

The resulting crude product was dissolved in a mixture of TFA/toluene (1:1, 1 mL) and heated to 70° C. for 1 h. The mixture was then cooled, concentrated and partitioned between aqueous 1M NaOH and EtOAc. The organic layer was dried over $Na_2SO_4$, filtered, and concentrated. The resulting crude oil was purified by silica gel chromatography (gradient elution, 1:1 hexanes:EtOAc to EtOAc) to yield Ex.4 (40 mg) as a white solid: $^1$H NMR (300 MHz, $CD_3OD$) δ7.37 (m, 5 H), 7.16 (d, 2 H), 7.00 (m, 4 H), 6.90 (d, 1 H), 4.46 (s, 2 H) ppm; mass spectrum m/z 317 [(M+H)$^+$; calcd for $C_{20}H_{17}N_2O_2$: 317].

Scheme 4

Compounds of this invention can be prepared by the following general procedure, scheme 4:

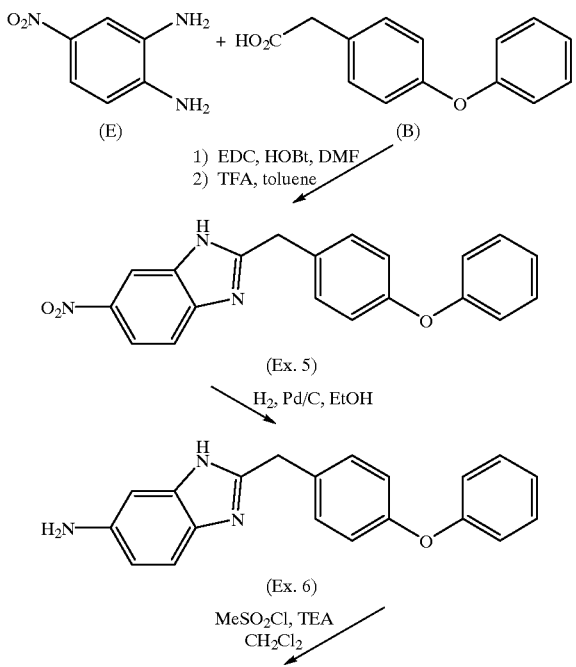

Example 5

6-Nitro-2-(4-phenoxy-benzyl)-1H-benzimidazole

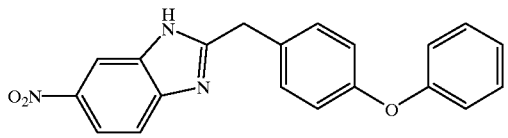
(Ex. 5)

Example 5 was prepared by the following procedure. To a solution of (4-phenoxy-phenyl)-acetic acid (B) (2.0 g, 8.8 mmol) in DMF (10 mL) was added EDC (1.8 g, 9.6 mmol), HOBt (1.3 g, 9.6 mmol) and 4-nitrophenylenediamine (E) (1.3 g, 8.8 mmol). The resulting reaction mixture was stirred at room temperature for 30 min followed by quenching with aqueous $NaHCO_3$ and EtOAc. The layers were separated and the organic layer was washed twice with water, dried over $Na_2SO_4$, filtered, and concentrated.

The resulting crude product was dissolved in a mixture of TFA/toluene (1:1, 10 mL) and heated to 70° C. for 1 h. The mixture was cooled, concentrated, and partitioned between aqueous 1 M NaOH and EtOAc. The organic layer was dried over $Na_2SO_4$, filtered, and concentrated. The resulting crude oil was purified by silica gel chromatography (gradient elution, 1:1 hexanes:EtOAc to EtOAc) to yield Ex.5 (2.0 g) as a white solid: $^1$H NMR (300 MHz, $CD_3OD$) δ8.55 (s, 1 H), 8.21 (d, 1 H), 7.71 (d, 1 H), 7.24 (m, 4 H), 7.07 (t, 1 H), 6.88 (d, 2 H), 6.79 (d, 2 H), 4.45 (s, 2 H) ppm; mass spectrum m/z 346 [(M+H)$^+$; calcd for $C_{20}H_{16}N_3O_3$: 346].

Example 6

2-(4-Phenoxy-benzyl)-3H-benzimidazol-5-ylamine

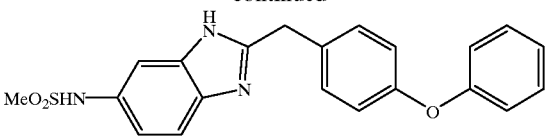
(Ex. 6)

Example 6 was prepared by the following procedure. To a solution of Ex. 5 (1.09 g, 3.16 mmol) in ethanol (15 mL) was added Pd/C (200 mg). The mixture was stirred at room temperature under a balloon of hydrogen gas for 30 min. The resulting reaction mixture was filtered through celite and the catalyst washed with EtOH. The filtrate was concentrated to yield Ex. 6 as a yellow solid (965 mg): $^1$H NMR (300MHz, $CDCl_3$) δ7.21 (m, 6 H), 7.03 (t, 1 H), 6.87 (d, 2 H), 6.73 (d, 2 H), 6.63 (s, 1 H), 6.57 (d, 1 H), 4.19 (s, 2 H) ppm; mass spectrum m/z 316 [(M+H)$^+$; calcd for $C_{20}H_{18}N_3O$: 316].

Example 7

N-[2-(4-Phenoxy-benzyl)-3H-benzimidazol-5-yl]-methanesulfonamide (Ex. 7)

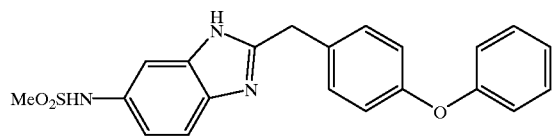

Example 7 was prepared by the following procedure. To a solution of Ex. 6 (25 mg, 0.08 mmol) in dichloromethane (1 mL) was added triethylamine (11 μL, 0.08 mmol) and methane sulfonylchloride (6 μL, 0.08 mmol). The resulting mixture was stirred at room temperature for 15 min and then quenched with EtOAc and NaHCO$_3$. The organic layer was dried over Na$_2$SO$_4$, filtered, and concentrated. The resulting crude product was purified by reverse phase HPLC to give Ex. 7 as a white solid (20 mg): $^1$H NMR (300 MHz, CD$_3$OD$_3$) δ7.69 (m, 2 H), 7.38 (m, 5 H), 7.17 (t, 1 H), 7.03 (m, 4 H), 4.51 (s, 2 H), 2.98 (s, 3 H) ppm; mass spectrum m/z 394 [(M+H)$^+$; calcd for C$_{21}$H$_{20}$N$_3$SO$_3$: 394].

All compounds analogous to Ex. 7 were prepared from aniline Ex. 6 via the above procedure using the appropriate sulfonyl chloride and purified by reverse-phase HPLC.

Examples 8–13

The following examples were similarly prepared by the general procedures described above.

Examples 8 and 8a

Ethanesulfonic acid[2-(4-phenoxy-benzyl)-3H-benzimidazol-5-yl]amide (Ex. 8)

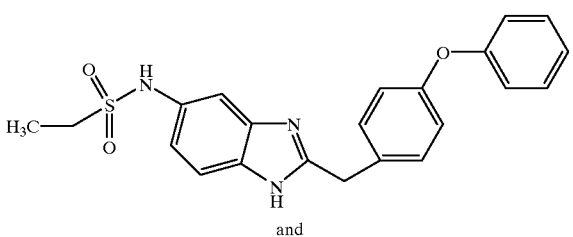

and (Ex. 8a)

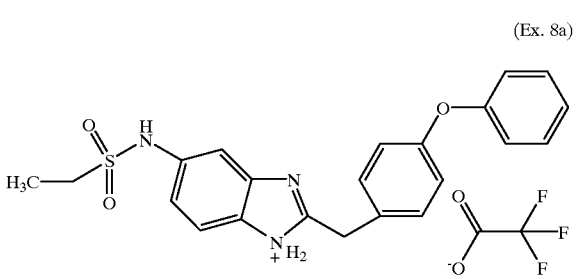

Example 8 was prepared by following the above procedure for Example 7 except using ethanesulfonyl chloride instead of methanesulfonyl chloride.

Example 9

Propane-1-sulfonic acid[2-(4-phenoxy-benzyl)-3H-benzimidazol-5-yl]amide (Ex. 9)

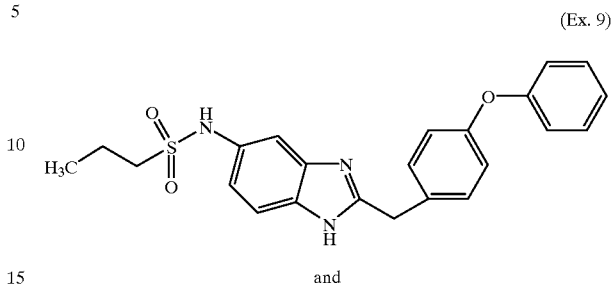

and (Ex. 9a)

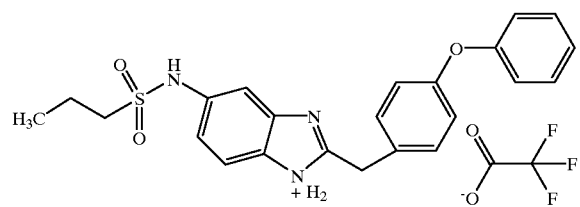

Example 9 was prepared by following the above procedure for Example 7 except using n-propanesulfonyl chloride instead of methanesulfonyl chloride.

Example 10

Butane-1-sulfonic acid[2-(4-phenoxy-benzyl)-3H-benzimidazol-5-yl]amide (Ex. 10)

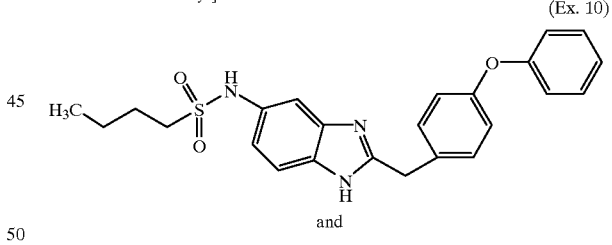

and (Ex. 10a)

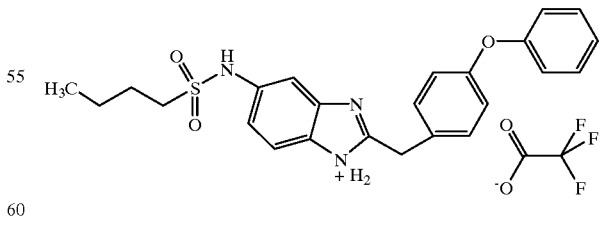

Example 10 was prepared by following the above procedure for Example 7 except using n-butanesulfonyl chloride instead of methanesulfonyl chloride.

Example 11

Thiopene-2-sulfonic acid[2-(4-phenoxy-benzyl)-3H-benzimidazol-5-yl]amide (Ex. 11)

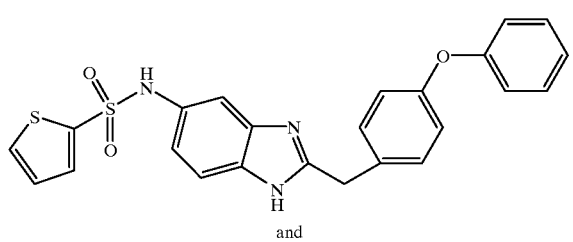

and (Ex. 11a)

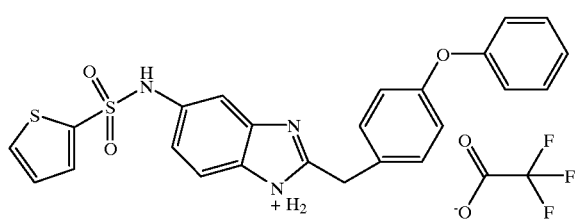

Example 11 was prepared by following the above procedure for Example 7 except using 2-thiophenesulfonyl chloride instead of methanesulfonyl chloride.

Example 12

1-Methyl-1H-imidazole-4-sulfonic acid[2-(4-phenoxy-benzyl)-3H-benzimidazol-5-yl]amide (Ex. 12)

and (Ex. 12a)

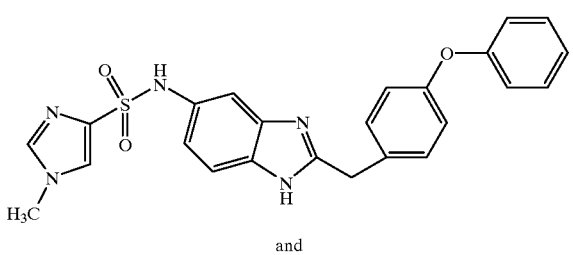

Example 12 was prepared by following the above procedure for Example 7 except using 1-methyl-1H-imidazao-4-sulfonyl chloride instead of methanesulfonyl chloride.

Example 13

N-[2-(4-phenoxy-benzyl)-3H-benzimidazol-5-yl]benzenesulfonamide (Ex. 13)

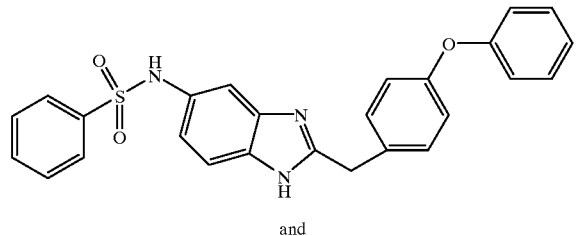

and (Ex. 13a)

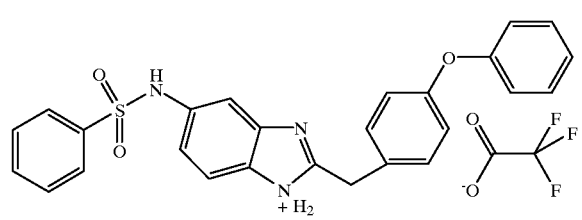

Example 13 was prepared by following the above procedure for Example 7 except using phenylsulfonyl chloride instead of methanesulfonyl chloride.

Examples 14–39

The following examples were similarly prepared by the general procedures described above.

Example 14

2-Methyl-N-[2-(4-phenoxybenzyl)-1H-benzimidazol-5-yl]benzenesulfonamide

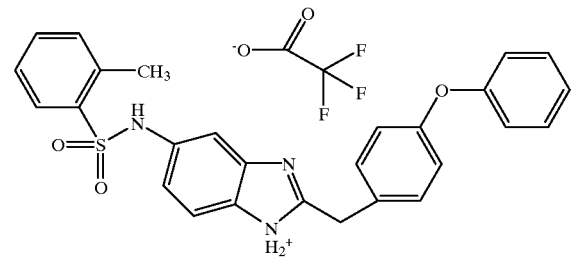

Example 14 was prepared by following the above procedure for Example 7 except using ortho-toluylsulfonyl chloride instead of methanesulfonyl chloride.

Example 15

3-Methyl-N-[2-(4-phenoxybenzyl)-1H-benzimidazol-5-yl]benzenesulfonamide

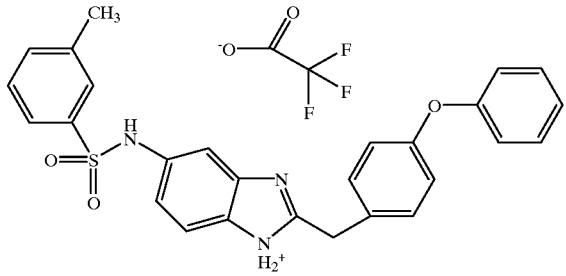

Example 15 was prepared by following the above procedure for Example 7 except using meta-toluylsulfonyl chloride instead of methanesulfonyl chloride.

Example 16

4-methyl-N-[2-(4-phenoxybenzyl)-1H-benzimidazol-5-yl]benzenesulfonamide

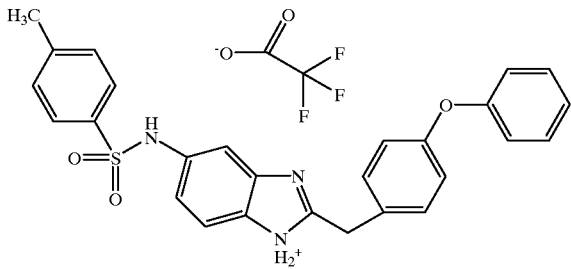

Example 16 was prepared by following the above procedure for Example 7 except using para-toluylsulfonyl chloride instead of methanesulfonyl chloride.

Example 17

3-Chloro-N-[2-(4-phenoxybenzyl)-1H-benzimidazol-5-yl]benzenesulfonamide

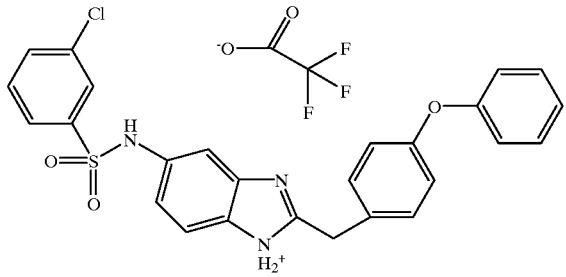

Example 17 was prepared by following the above procedure for Example 7 except using 3-chloro-phenylsulfonyl chloride instead of methanesulfonyl chloride.

Example 18

4-Chloro-N-[2-(4-phenoxybenzyl)-1H-benzimidazol-5-yl]benzenesulfonamide

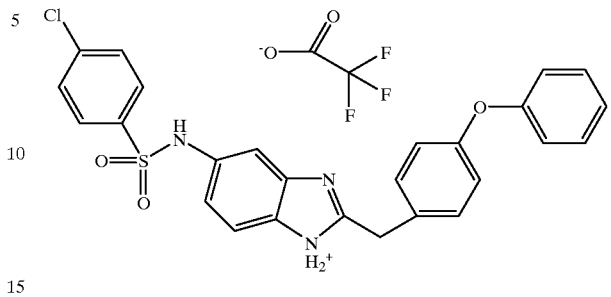

Example 18 was prepared by following the above procedure for Example 7 except using 4-chloro-phenyl sulfonyl chloride instead of methanesulfonyl chloride.

Example 19

2-Fluoro-N-[2-(4-phenoxybenzyl)-1H-benzimidazol-5-yl]benzenesulfonamide

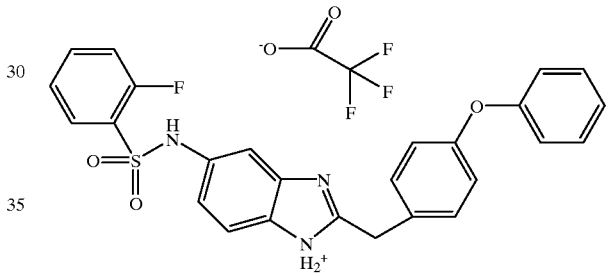

Example 19 was prepared by following the above procedure for Example 7 except using 2-fluoro-phenylsulfonyl chloride instead of methanesulfonyl chloride.

Example 20

4-Fluoro-N-[2-(4-phenoxybenzyl)-1H-benzimidazol-5-yl]benzenesulfonamide

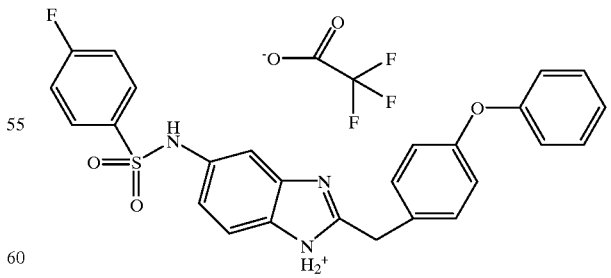

Example 20 was prepared by following the above procedure for Example 7 except using 4-fluoro-phenyl sulfonyl chloride instead of methanesulfonyl chloride.

Example 21

4-Methoxy-N-[2-(4-phenoxybenzyl)-1H-benzimidazol-5-yl]benzenesulfonamide

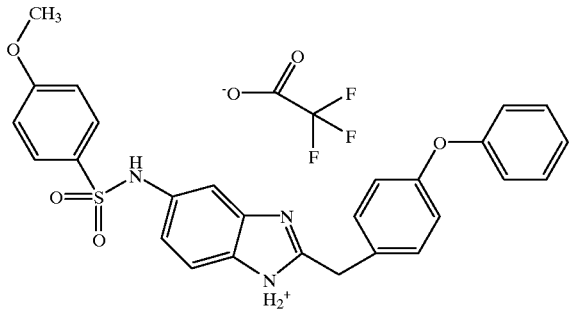

Example 21 was prepared by following the above procedure for Example 7 except using 4-methoxy-phenylsulfonyl chloride instead of methanesulfonyl chloride.

Example 22

N-[2-(4-phenoxybenzyl)-1H-benzimidazol-5-yl]-2-(trifluoromethoxy)benzenesulfonamide

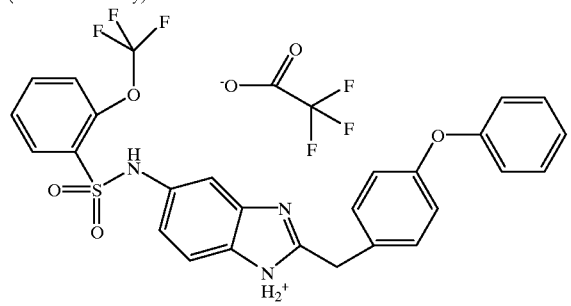

Example 22 was prepared by following the above procedure for Example 7 except using 2-trifluoromethoxy-phenylsulfonyl chloride instead of methanesulfonyl chloride.

Example 23

N-[2-(4-phenoxybenzyl)-1H-benzimidazol-5-yl]-2-(trifluoromethyl)benzenesulfonamide

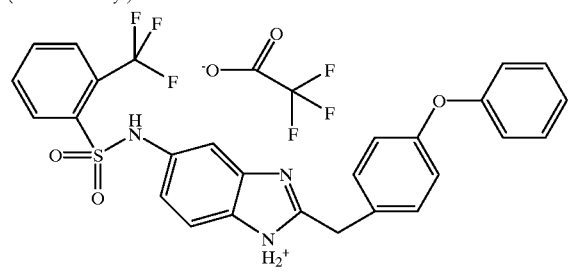

Example 23 was prepared by following the above procedure for Example 7 except using 2-trifluoromethyl-phenylsulfonyl chloride instead of methanesulfonyl chloride.

Example 24

N-[2-(4-phenoxybenzyl)-1H-benzimidazol-5-yl]-4-(trifluoromethyl)benzenesulfonamide

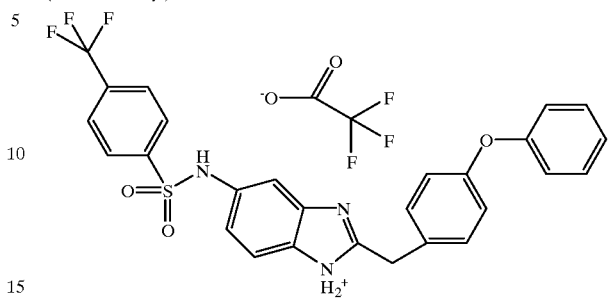

Example 24 was prepared by following the above procedure for Example 7 except using 3-trifluoromethyl-phenylsulfonyl chloride instead of methanesulfonyl chloride.

Example 25

3,5-Dimethyl-N-[2-(4-phenoxybenzyl)-1H-benzimidazol-5-yl]isoxazole-4-sulfonamide

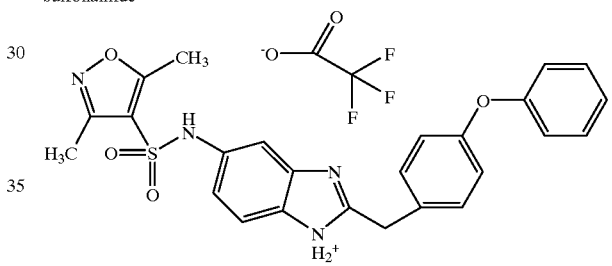

Example 25 was prepared by following the above procedure for Example 7 except using 3,5-dimethyl-isoxazole-4-sulfonyl chloride instead of methanesulfonyl chloride.

Example 26

N-[2-(4-phenoxybenzyl)-1H-benzimidazol-5-yl]-5-(phenylsulfonyl)thiophene-2-sulfonamide

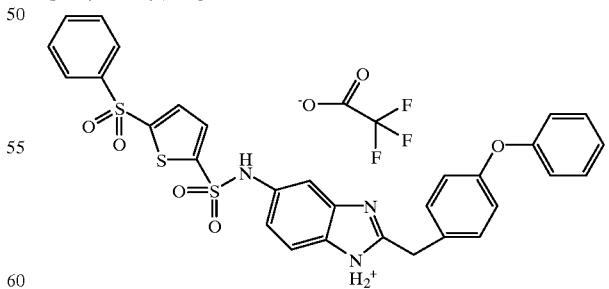

Example 26 was prepared by following the above procedure for Example 7 except using 5-benzenesulfonyl-thiophene-2-sulfonyl chloride instead of methanesulfonyl chloride.

Example 27

2,5-Dichloro-N-[2-(4-phenoxybenzyl)-1H-benzimidazol-5-yl]thiophene-3-sulfonamide

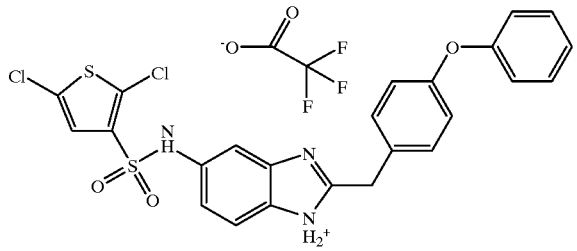

Example 27 was prepared by following the above procedure for Example 7 except using 2,5-dichloro-3-thiophenesulfonyl chloride instead of methanesulfonyl chloride.

Example 28

N-[2-(4-phenoxybenzyl)-1H-benzimidazol-5-yl]acetamide

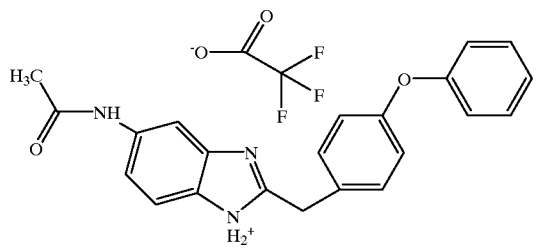

Example 28 was prepared by following the above procedure for Example 7 except using acetyl chloride instead of methanesulfonyl chloride.

Example 29

1,1,1-Trifluoro-N-[2-(4-phenoxybenzyl)-1H-benzimidazol-5-yl]methanesulfonamide

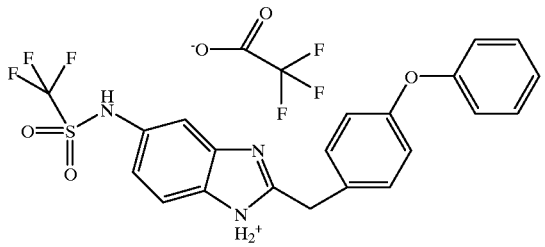

Example 29 was prepared by following the above procedure for Example 7 except using trifluoromethylsulfonyl chloride instead of methanesulfonyl chloride.

Example 30

1-Chloro-N-[2-(4-phenoxybenzyl)-1H-benzimidazol-5-yl]methanesulfonamide

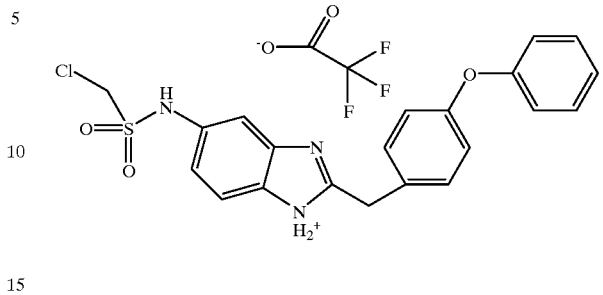

Example 30 was prepared by following the above procedure for Example 7 except using chloromethylsulfonyl chloride instead of methanesulfonyl chloride.

Example 31

2-(6-Hydroxy-3-oxo-3H-xanthen-9-yl)-5-[({[2-(4-phenoxybenzyl)-1H-benzimidazol-5-yl]amino}carbonothioyl)amino]benzoic acid

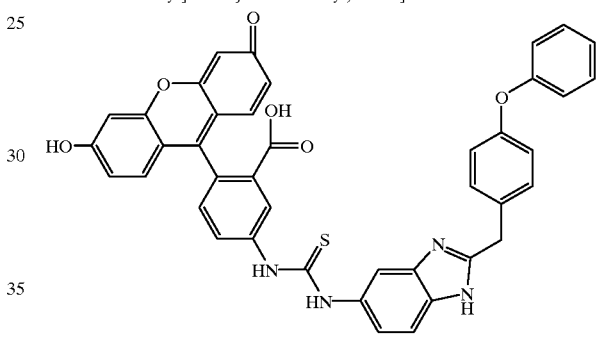

Example 31 was prepared by following the above procedure for Example 7 except using fluoroscein-5-isothiocyanate instead of methanesulfonyl chloride.

Example 32

5-(Dimethylamino)-N-[2-(4-phenoxybenzyl)-1H-benzimidazol-5-yl]naphthalene-1-sulfonamide

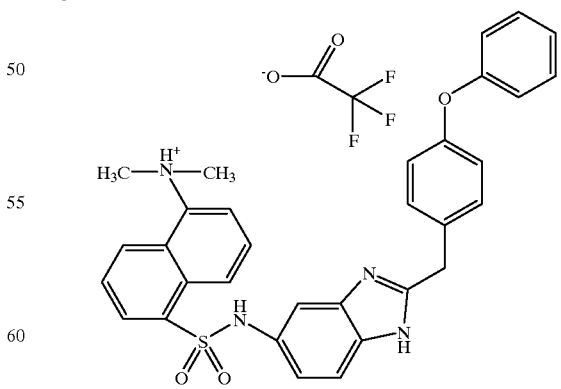

Example 32 was prepared by following the above procedure for Example 7 except using dansylsulfonyl chloride instead of methanesulfonyl chloride.

Example 33

2-(6-Hydroxy-3-oxo-3H-xanthen-9-yl)-4-[({[2-(4-phenoxybenzyl)-1H-benzimidazol-5-yl]amino}carbonothioyl)amino]benzoic acid

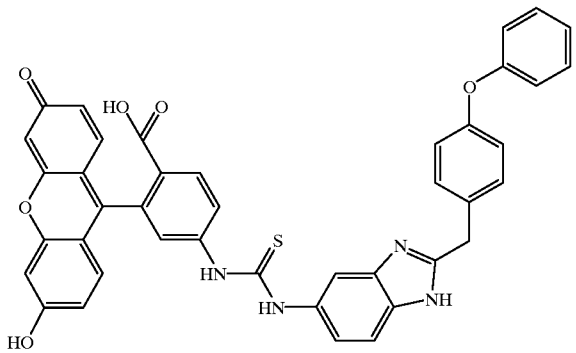

Example 33 was prepared by following the above procedure for Example 7 except using fluoroscein-6-isothiocyanate instead of methanesulfonyl chloride.

Example 34

2-(6-Hydroxy-3-oxo-3H-xanthen-9-yl)-4-{[[(6-oxo-6-{[2-(4-phenoxybenzyl)-1H-benzimidazol-5-yl]amino}hexyl)amino]carbonyl}benzoic acid (Ex. 34a)

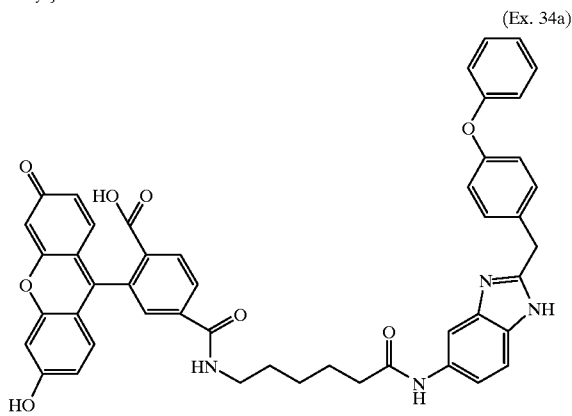

2-(6-Hydroxy-3-oxo-3H-xanthen-9-yl)-5-{[[(6-oxo-6-{[2-(4-phenoxybenzyl)-1H-benzimidazol-5-yl]amino}hexyl)amino]carbonyl}benzoic acid (Ex. 34b)

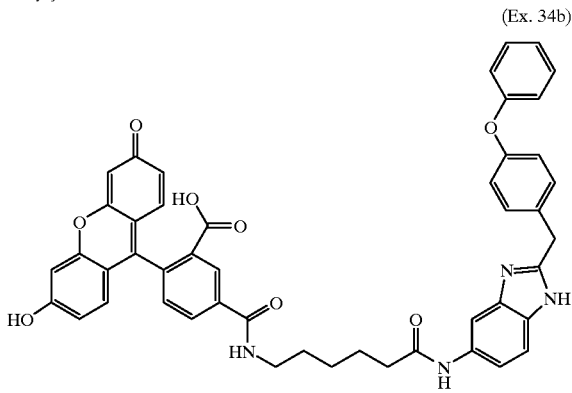

Example 34 (34a and 34b) was prepared by following the above procedure for Example 7 except using 6-(fluoroscein-5-(and-6)-carboxamido)hexanoic acid, succinimidyl ester (mixed isomers) instead of methanesulfonyl chloride.

Example 35

N-[2-(4-phenoxybenzyl)-1H-benzimidazol-5-yl]propane-2-sulfonamide

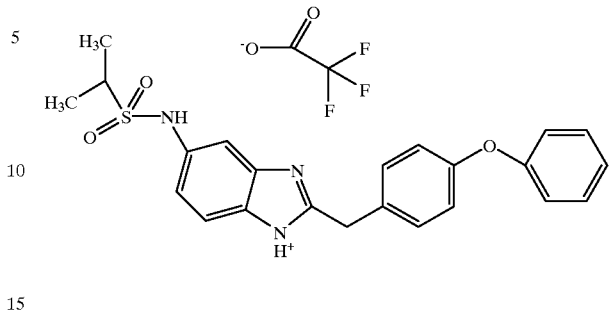

Example 35 was prepared by following the above procedure for Example 7 except using isopropylsulfonyl chloride instead of methanesulfonyl chloride.

Example 36

(E)-N-[2-(4-phenoxybenzyl)-1H-benzimidazol-5-yl]-2-phenylethene-sulfonamide

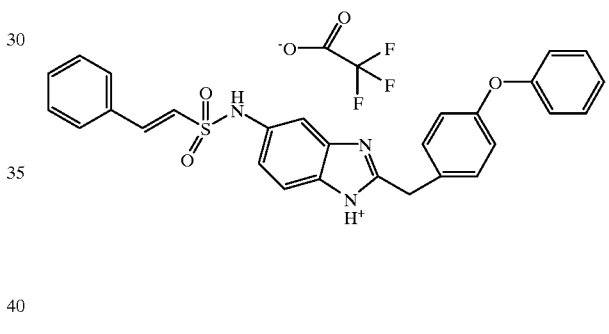

Example 36 was prepared by following the above procedure for Example 7 except using styrylsulfonyl chloride instead of methanesulfonyl chloride.

Example 37

N-[2-(4-phenoxybenzyl)-1H-benzimidazol-5-yl]butane-2-sulfonamide

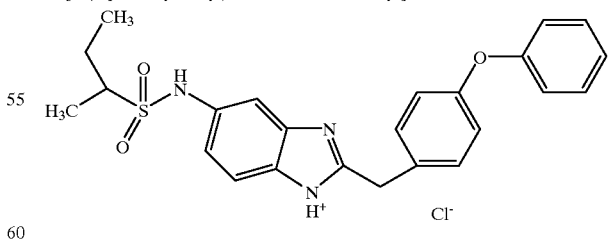

Example 37 was prepared by following the above procedure for Example 7 except using butane-2-sulfonyl chloride instead of methanesulfonyl chloride.

Example 38

2-Methyl-N-[2-(4-phenoxybenzyl)-1H-benzimidazol-5-yl]prop-1-ene-1-sulfonamide

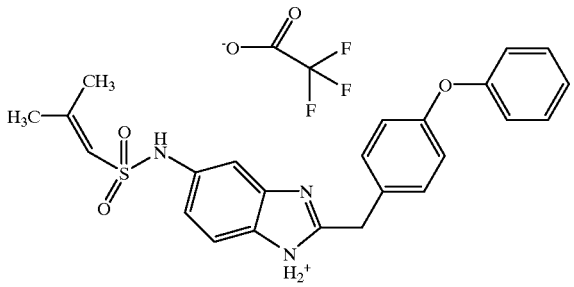

Example 38 was prepared by following the above procedure for Example 7 except using 2-methyl-propene-1-sulfonyl chloride instead of methanesulfonyl chloride.

Example 39

2-Methyl-N-[2-(4-phenoxybenzyl)-1H-benzimidazol-5-yl]propane-1-sulfonamide

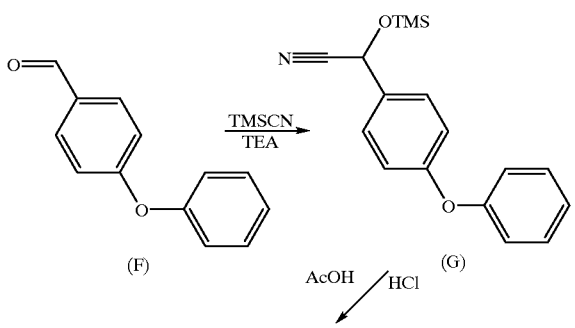

Example 39 was prepared by following the above procedure for Example 7 except using 2-methyl-propane-1-sulfonyl chloride instead of methanesulfonyl chloride.

Scheme 5

Compounds of this invention can be prepared by the following general procedure, scheme 5:

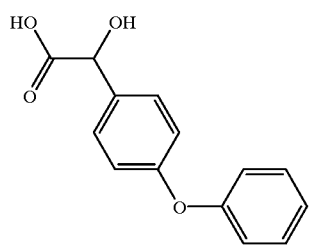

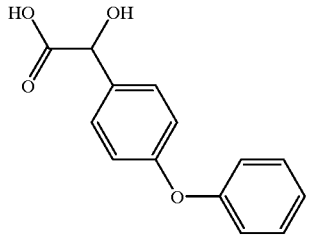

(H)

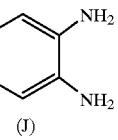

(J)

1) EDC, HOAt, DMF
2) AcOH

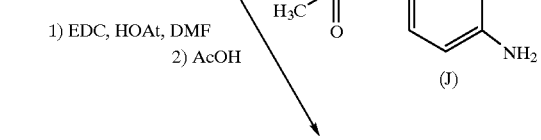

Ex. 40

TPAP, NMO

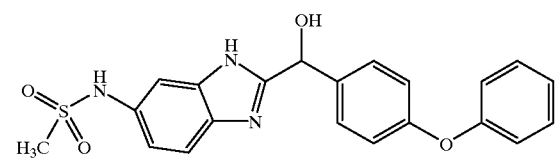

Ex. 41

Preparation of Hydroxy-acid Compound (H)

Hydroxy(4-phenoxyphenyl)acetic acid

Compound (H)

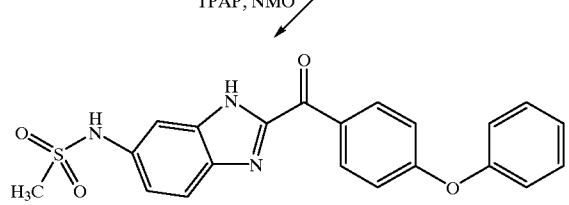

To a 0° C. solution of 4-phenoxy benzaldehyde (F) (1.00 g, 5.04 mmol) and trimethylsilyl cyanide (0.63 mL, 5.04 mmol) in dichloromethane (20 mL) was added triethylamine (0.07 mL, 0.5 mmol). The reaction mixture was stirred at 0° C. for 3 h and then concentrated to give (4-phenoxyphenyl)-trimethylsilanyloxy-acetonitrile (G) as a clear oil. This protected cyanohydrin (G) was used without further purification.

The above cyanohydrin (G) (0.1 g, 0.3 mmol) was heated to 130° C. in a solution of acetic acid (1 mL) and HCl (6N, 2 mL) for 1 h. The reaction mixture was cooled, concentrated and the crude solid recrystallized from toluene to give the hydroxy acid (H) as a white solid: $^1$H NMR (300 MHz, CD$_3$OD) δ7.42 (d, 2 H), 7.38 (7, 2 H), 7.10 (t, 1 H), 6.98 (7, 4 H), 5.15 (s, 1 H) ppm; mass spectrum m/z 245 [(M+H)$^+$; calcd for C$_{14}$H$_{13}$O$_4$: 245].

Example 40

N-{2-[hydroxy(4-phenoxyphenyl)methyl]-1H-benzimidazol-6-yl}methanesulfonamide

Ex. 40

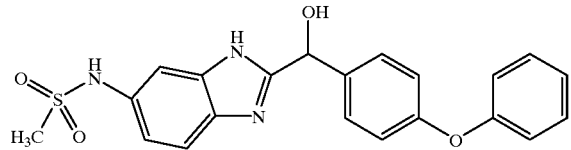

Example 40 was prepared by the following procedure: To a solution of hydroxy acid (H) (80 mg, 0.33 mmol) in DMF (2 mL) was added EDC (63 mg, 0.33 mmol), HOAt (45 mg, 0.33 mmol) and methanesulfonic acid (3,4-diaminophenyl)-amide (J) (66 mg, 0.33 mmol). The reaction mixture was stirred at room temperature for 2 h followed by quenching with aqueous NaHCO$_3$ and EtOAc. The layers were separated and the organic was washed twice with water, dried over Na$_2$SO$_4$, filtered and concentrated.

The crude product was dissolved in acetic acid (5 mL) and heated to 130° C. for 15 min. The reaction mixture was cooled, concentrated and partitioned between aqueous NaHCO$_3$ and EtOAc and the organic layer was dried over Na$_2$SO$_4$, filtered and concentrated. The crude oil was purified by silica gel chromatography (gradient elution, 95:5:0.5 to 80:20:2 dichloromethane:methanol: NH4OH) to give Example40 as a yellow oil: $^1$H NMR (300 MHz, CD$_3$OD) δ7.55–7.48 (m, 4 H), 7.30 (t, 2 H), 7.18–7.04 (m, 2 H), 6.95 (d, 4 H), 5.98 (s, 1 H); 2.84 (s, 3 H) ppm; mass spectrum m/z 410 [(M+H)$^+$; calcd for C$_{21}$H$_{19}$N$_3$O$_4$S: 401].

Example 42

N-{2-[hydroxy(4-phenoxyphenyl)methyl]-1H-benzimidazol-6-yl}ethanesulfonamide

Ex. 42

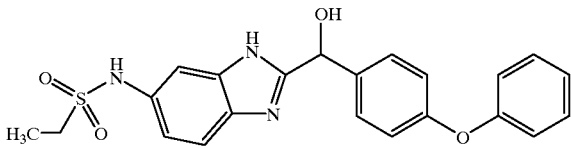

Example 42 was prepared by following the above procedure for Example 40 except using ethanesulfonic acid (3,4-diamino-phenyl)-amide instead of methanesulfonic acid (3,4-diamino-phenyl)-amide: mass spectrum m/z 425 [(M+H)$^+$; calcd for C$_{22}$H$_{21}$N$_3$O$_4$S: 425].

Example 43

(6-Methoxy-1H-benzimidazol-2-yl)(4-phenoxyphenyl)methanol

Ex. 43

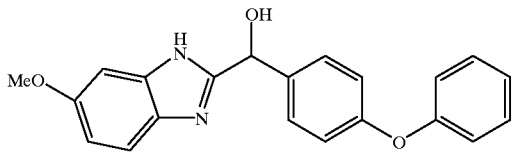

Example 43 was prepared by following the above procedure for Example 40 except using 4-methoxy-benzene-1,2-diamine instead of of methanesulfonic acid (3,4-diaminophenyl)-amide: mass spectrum m/z 347 [(M+H)$^+$; calcd for C$_{21}$H$_{19}$N$_2$O$_3$: 347].

Example 44

N-{2-[hydroxy(4-phenoxyphenyl)methyl]-1H-benzimidazol-6-yl}propane-2-sulfonamide Ex. 44

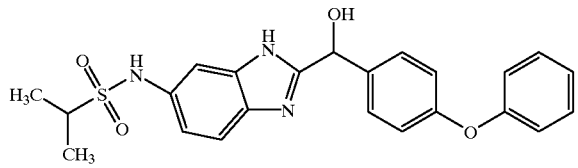

Example 44 was prepared by following the above procedure for Example40 except using of isopropylsulfonic acid (3,4-diamino-phenyl)-amide instead of of methanesulfonic acid (3,4-diamino-phenyl)-amide: mass spectrum m/z 438 [(M+H)$^+$; calcd for C$_{23}$H$_{24}$N$_3$O$_4$S: 438].

Example 42a and Example 42b

Racemate Example 42 was separated into its enantiomers by chiral HPLC on a Chiralpack AD column (250×4.6 cm) eluting with 60% hexane +0.1% diethylamine and 40% EtOAc. The faster eluting compound was Example 42a. The slower eluting compound was Example 42b.

Example 41

N-[2-(4-phenoxybenzoyl)-1H-benzimidazol-6-yl]methanesulfonamide

Ex. 41

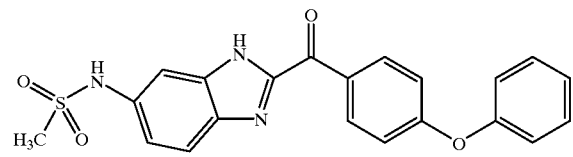

Example 41 was prepared by the following procedure: To a solution of Example 40 (100 mg, 0.2 mmol) in dichloromethane (5 mL) was added 4A sieves. To that mixture was added TPAP (5 mg) and NMO (43 mg, 0.36 mmol) and stirring was continued for 1 h. The reaction mixture was partitioned between EtOAc and water. The organic layer was dried over Na$_2$SO$_4$, filtered and concentrated. The crude oil was purified by reverse phase HPLC to give Example 41: mass spectrum m/z 408 [(M+H)$^+$; calcd for C$_{21}$H$_{18}$N$_3$O$_4$S: 408].

Example 45

N-methyl-N-[2-(4-phenoxybenzyl)-1H-benzimidazol-6-yl]methanesulfonamide

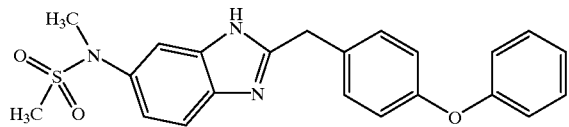

Ex. 45

Example 45 was prepared by the following procedure: To a solution of Example 7 (15 mg, 0.04 mmol) in DMF (1 mL) was added cesium carbonate (25 mg, 0.08 mmol) and methyl iodide (3 μL, 0.04 mmol). The reaction mixture was stirred at room temperature for 2 h followed by quenching with aqueous $NaHCO_3$ and EtOAc. The layers were separated and the organic was washed twice with water, dried over $Na_2SO_4$, filtered and concentrated. Purification on reverse phase HPLC gave Example 45: $^1$H NMR (300 MHz, $CDCl_3$) δ7.75 (s, 1 H), 7.64 (d, 1 H), 7.43 (dd, 1 H), 7.18–7.12 (m, 5 H), 7.05 (t, 1 H); 6.95 (t, 3 H); 4.42 (s, 2 H); 3.17 (s, 3 H); 281 (s, 3 H) ppm; mass spectrum m/z 408 [(M+H)$^+$; calcd for $C_{22}H_{22}N_3O_3S$: 408].

Scheme 6

Compounds of this invention can be prepared by the following general procedure, Scheme 6:

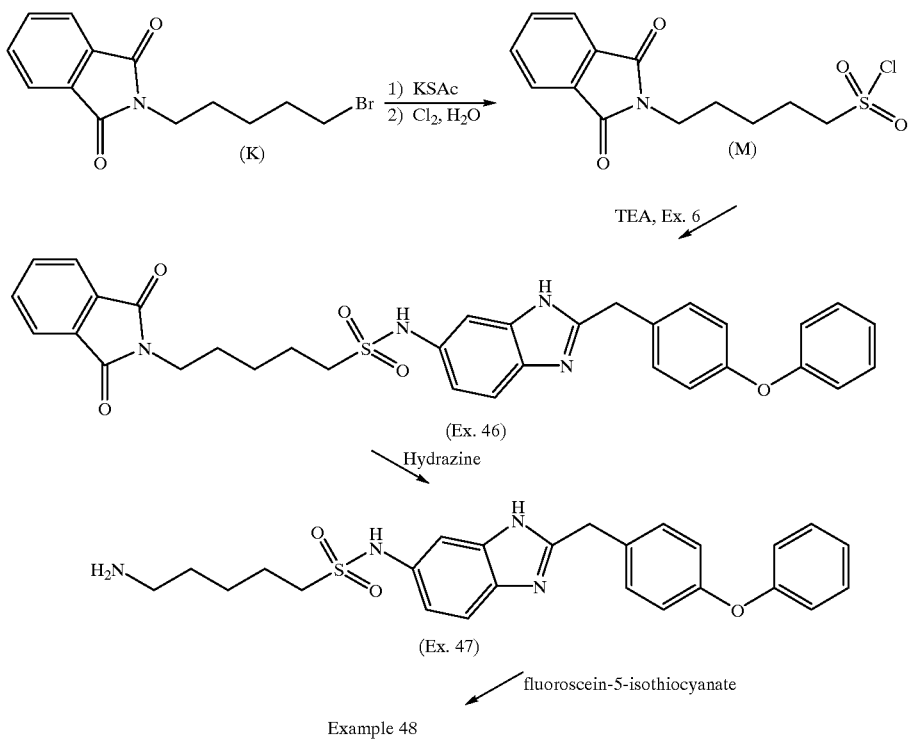

Example 46

5-(1,3-Dioxo-1,3-dihydro-2H-isoindol-2-yl)-N-[2-(4-phenoxybenzyl)-1H-benzimidazol-6-yl]pentane-1-sulfonamide Example 46

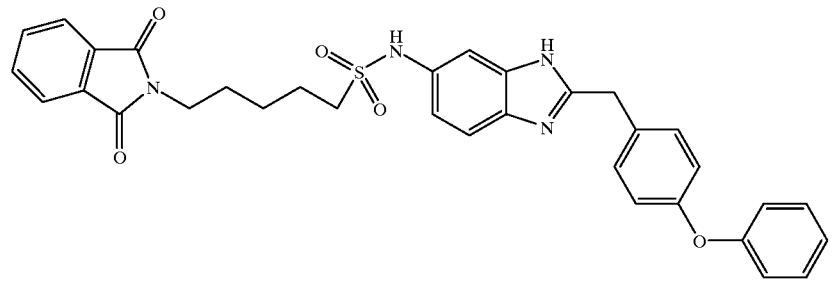

Example 46 was prepared by the following procedure: To a room temperature solution of bromide (K) (0.50 g, 1.69 mmol) in DMF (30 mL) was added potassium thioacetate (0.21 g, 1.86 mmol). The reaction mixture was stirred for 20 min and partitioned between EtOAc and water. The organic layer was dried over Na$_2$SO$_4$, filtered and concentrated to give thioacetic acid 5-(1,3-dioxo-1,3-dihydro-isoindol-2-yl)-pentyl ester (L) (not shown). Compound (L) was used without further purification.

Dissolved compound (L) (0.10 g, 0.34 mmol) in 4 ml of 1:1 EtOAc/H2O. The biphasic mixture was cooled to 0° C. and chlorine gas was bubbled through the mixture until it turned yellow (10 sec). The reaction mixture was partitioned between dichloromethane and water. The organic layer was dried over Na$_2$SO$_4$, filtered and concentrated to give 5-(1,3-dioxo-1,3-dihydro-isoindol-2-yl)-pentanesulfonyl chloride (M). Compound (M) was used without further purification.

mmol) in EtOH (0.5 mL) was added hydrazine (2 μL, 0.07 mmol) and the resulting reaction mixture was stirred for 4 h. The mixture was then partitioned between dichloromethane and aqueous NaHCO$_3$. The organic layer was dried over Na$_2$SO$_4$, filtered and concentrated to give Example 47 which was used without further purification: mass spectrum m/z 465 [(M+H)$^+$; calcd for C$_{25}$H$_{29}$N$_4$O$_5$S: 465].

Example 48

2-(6-Hydroxy-3-oxo-3H-xanthen-9-yl)-5-[({[5-({[2-(4-phenoxybenzyl)-1H-benzimidazol-6-yl]amino}sulfonyl)pentyl]amino}carbonothioyl)amino]benzoic acid Ex. 48

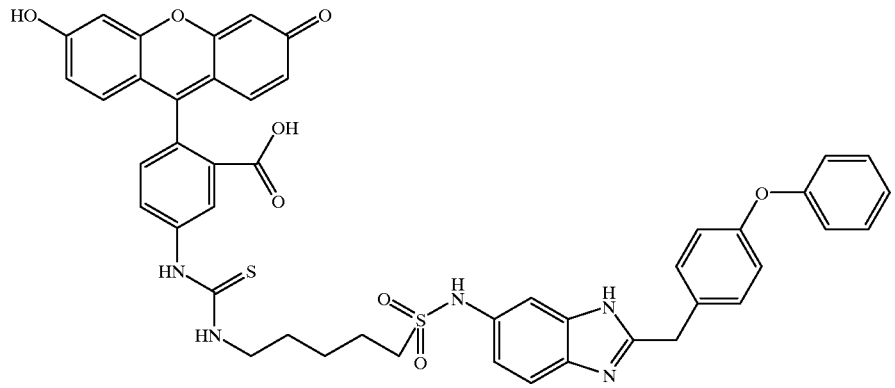

Example 46 was prepared by following the procedure for Example 7 except using 5-(1,3-dioxo-1,3-dihydro-isoindol-2-yl)-pentanesulfonyl chloride (M) instead of methanesulfonyl chloride: $^1$H NMR (400 MHz, CD$_3$OD) δ7.75–7.60 (m, 6 H), 7.35 (m, 5 H), 7.16 (t, 1 H), 6.99 (t, 4 H), 4.50 (s, 2 H); 3.55 (dd, 2 H); 3.10 (dd, 2 H); 1.79 (m, 2 H); 1.60 (m, 2 H); 1.40 (m, 2 H) ppm; mass spectrum m/z 595 [(M+H)$^+$; calcd for C$_{33}$H$_{31}$N$_4$O$_5$S: 595].

Example 47

5-Amino-N-[2-(4-phenoxybenzyl)-1H-benzimidazol-6-yl]pentane-1-sulfonamide

Ex. 47

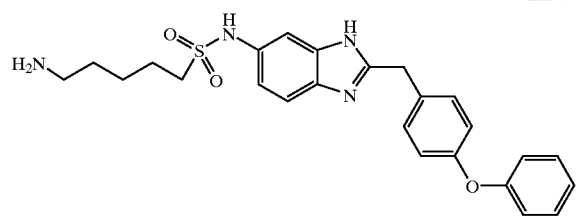

Example 47 was prepared by the following procedure: To a room temperature solution of Example 46 (10 mg, 0.013

Example 48 was prepared by the following procedure: To a room temperature solution of Example 47 (6 mg, 0.013 mmol) in dichloromethane (0.5 mL) and THF (0.5 mL) was added fluoroscein-5-isothiocyanate (5 mg, 0.02 mmol) and triethylamine (2 μL). The resulting reaction mixture was stirred for 48 h, concentrated and purified by reverse phase HPLC to give Example 48: mass spectrum m/z 854 [(M+H)$^+$; calcd for C$_{46}$H$_{40}$N$_5$O$_8$S$_2$: 854].

Example 49

N-[5-({[2-(4-phenoxybenzyl)-1H-benzimidazol-6-yl]amino}sulfonyl)pentyl]acetamide

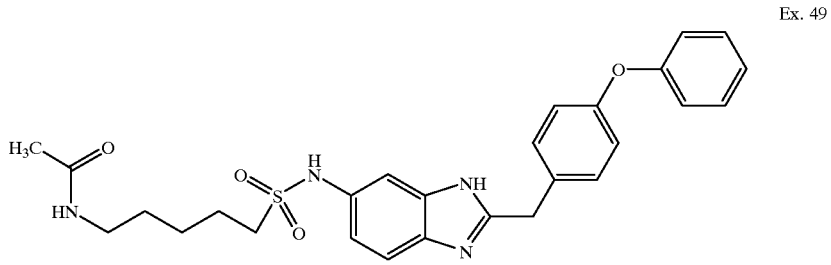

Ex. 49

Example 49 was prepared by the following procedure: To a 140° C. solution of Example 47 (20 mg, 0.043 mmol) in acetic acid (2 mL) was added acetic anhydride (0.3 mL) and the mixture was stirred for 1 h. The resulting reaction mixture was concentrated and then purified by reverse phase HPLC to give Example 49: $^1$H NMR (300 MHz, CD$_3$OD) δ7.70 (m, 2 H), 7.39 (m, 5 H), 7.18 (t, 1 H), 7.02 (t, 4 H), 4.50 (s, 2 H); 3.10 (m, 4 H); 1.90 (s, 3 H); 1.79 (m, 2 H); 1.40 (m, 4 H) ppm; mass spectrum m/z 507 [(M+H)$^+$; calcd for C$_{27}$H$_{31}$N$_4$O$_4$S: 507].

Scheme 7

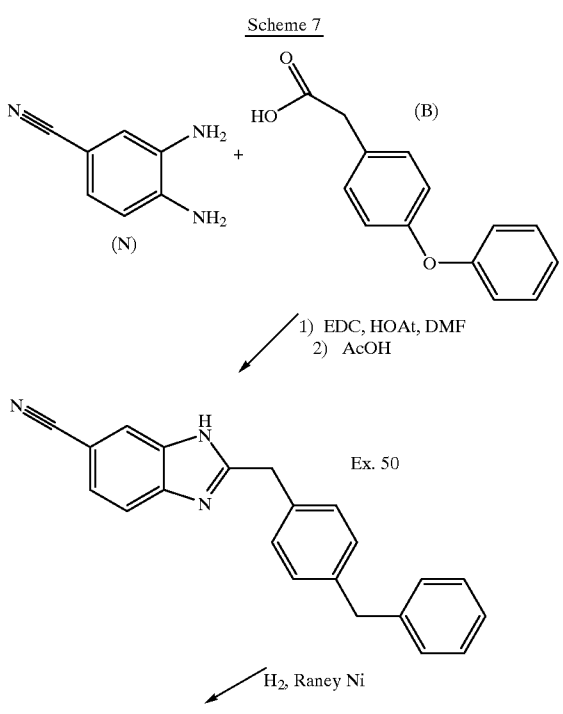

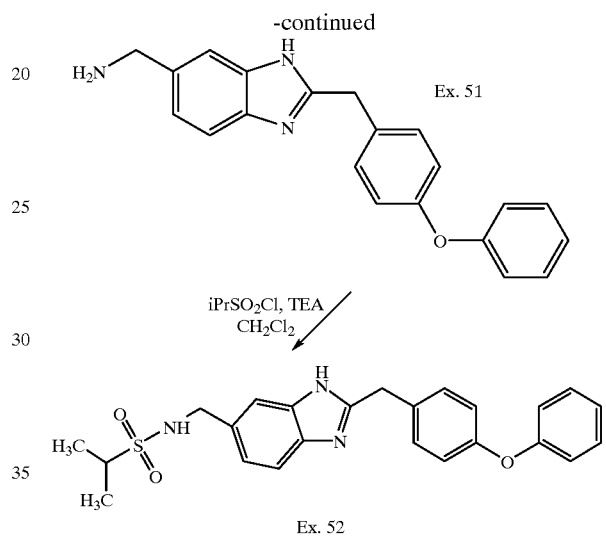

Example 50

2-(4-Phenoxybenzyl)-1H-benzimidazole-6-carbonitrile

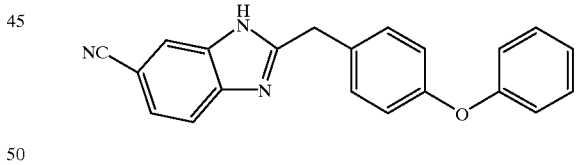

Ex. 50

Example 50 was prepared by the following procedure: To a solution of acid (B) (3.0 g, 13.1 mmol) in DMF (40 mL) was added EDC (2.8 g, 14.5 mmol), HOAt (1.9 g, 14.5 mmol) and 3,4-diaminobenzonitrile (N) (1.75 g, 13.1 mmol). The resulting reaction mixture was stirred at room temperature for 30 min followed by quenching with aqueous NaHCO$_3$ and EtOAc. The layers were separated and the organic was washed twice with water, dried over Na$_2$SO$_4$, filtered and concentrated.

The crude product was dissolved in acetic acid (30 mL) and heated to 130° C. for 30 min. The reaction mixture was cooled, concentrated and partitioned between aqueous NaHCO$_3$ and EtOAc and the organic layer was dried over Na$_2$SO$_4$, filtered and concentrated. The crude oil was purified by silica gel chromatography (gradient elution, 10%

EtOAc/hexanes to EtOAc) followed by trituration with 5% EtOAc/hexanes to give Example 50 as a pink solid: $^1$H NMR (300 MHz, DMSO-$d_6$) δ8.04 (s, 1 H); 7.62 (d, 2 H), 7.58 (d, 2 H), 7.37 (m, 4 H), 7.11 (t, 1 H); 6.96 (m, 4 H), 4.11 (s, 2 H) ppm; mass spectrum m/z 326 [(M+H)$^+$; calcd for $C_{21}H_{16}N_3O$: 326].

Example 51

1-[2-(4-Phenoxybenzyl)-1H-benzimidazol-6-yl]methanamine

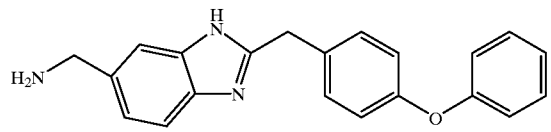

Ex. 51

Example 51 was prepared by the following procedure: To a solution of Example 50 (0.3 g, 0.92 mmol) in EtOH (20 mL) was added Raney Ni (0.05 g). The resulting reaction mixture was stirred under a balloon of hydrogen. After 1 h, more catalyst (0.05 g) was added. After a further 1 h, the reaction mixture was filtered through celite and the crude product purified by silica gel chromatography (gradient elution: 95;5;0.5 to 80:20:2 dichloromethane:methanol:NH4OH to give Example 51: mass spectrum m/z 330 [(M+H)$^+$; calcd for $C_{21}H_{20}N_3O$: 330].

Example 52

N-{[2-(4-phenoxybenzyl)-1H-benzimidazol-6-yl]methyl}propane-2-sulfonamide

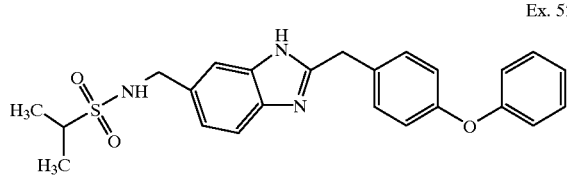

Ex. 52

Example 52 was prepared by the following procedure: To a solution of Example 51 (0.2 g, 0.61 mmol) in pyridine (5 mL) was added isopropylsulfonyl chloride (0.17 g, 1.21 mmol). The resulting reaction mixture was heated to 100° C. for 5 min, cooled and concentrated. This was followed by purification by reverse phase HPLC. Repurification by silica gel chromatography (isocratic elution, 95:5:0.5 dichloromethane:methanol:NH4OH) gave Example 52: mass spectrum m/z 436 [(M+H)$^+$; calcd for $C_{24}H_{26}N_3O_3S$: 330].

Scheme 8

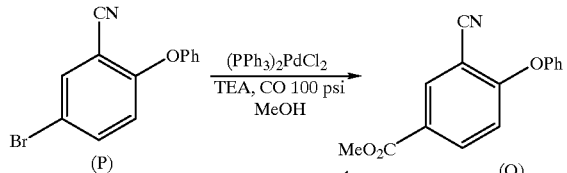

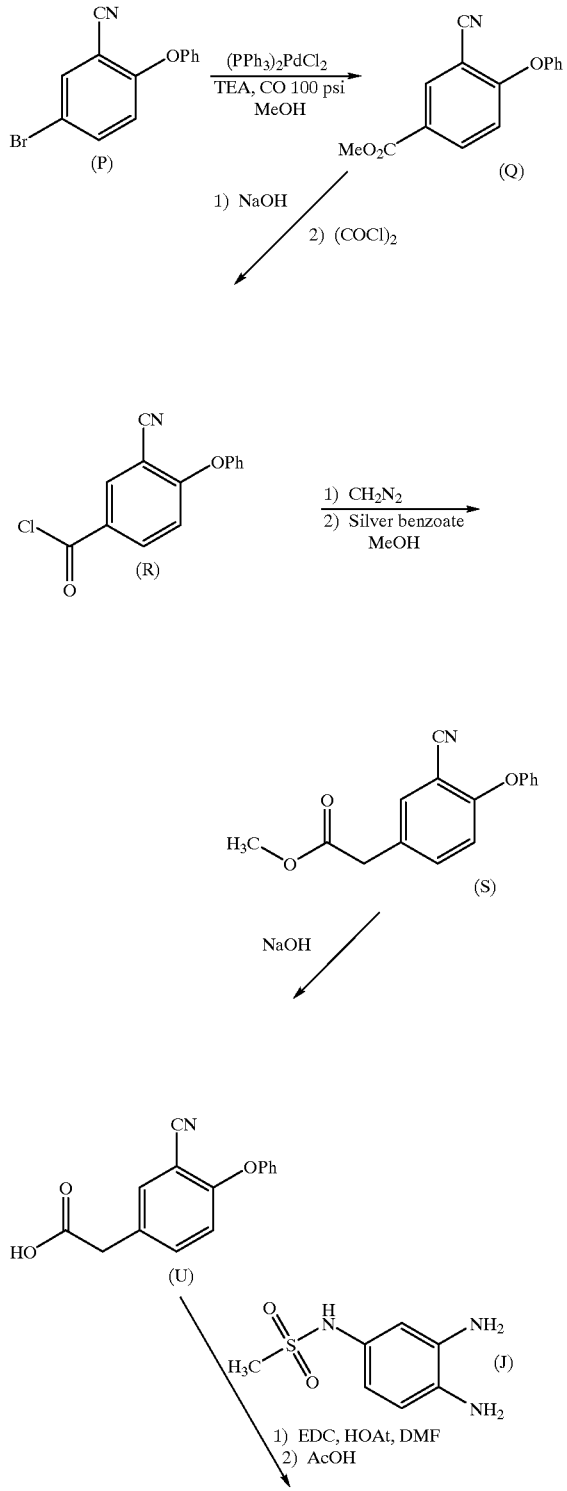

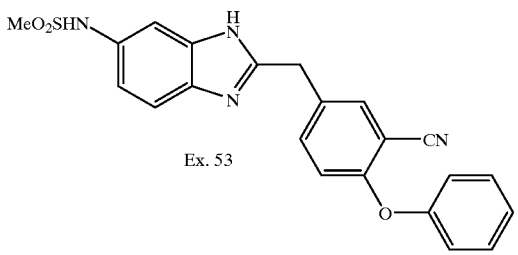

Ex. 53

Example 53

N-[2-(3-cyano-4-phenoxybenzyl)-1H-benzimidazol-6-yl]
methanesulfonamide

Ex. 53

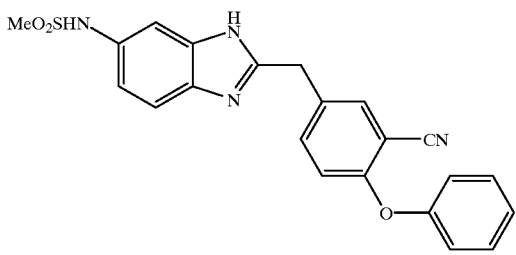

Example 53 was prepared by the following procedure: A solution of 2-phenoxy-5-bromobenzonitrile (0.2 g, 0.73 mmol), (PPh$_3$)$_2$PdCl$_2$ (0.05 g) and triethylamine (0.05 mL) in MeOH (10 mL) was placed in a pressure bomb and filled with CO gas at 100 psi. The reaction mixture was heated to 100° C. for 15 h, cooled and partitioned between EtOAc and H$_2$O. The organic layers was dried over Na$_2$SO$_4$, filtered, concentrated and purified by silica gel chromatography (gradient elution 9:1 hexanes:EtOAc to EtOAc) to give methyl ester (Q): $^1$H NMR (300 MHz, CDCl$_3$) δ8.35 (d, 1 H); 8.10 (dd, 1 H), 7.45 (t, 2 H), 7.30 (t, 1 H), 7.15 (d, 2 H); 6.81 (d, 1 H), 3.96 (s, 3 H) ppm.

Compound (Q) (50 mg, 0.2 mmol) was suspended in NaOH (1M, 3 ml) and was heated to 120° C. Methanol was added until the compound dissolved. The reaction mixture was cooled and partitioned between EtOAc and H$_2$O. The organic layers was dried over Na$_2$SO$_4$, filtered, and concentrated to give the corresponding acid.

The above acid was dissolved in dichloromethane (1 mL). DMF (2 μL) and (COCl)$_2$ (9 μL) was added and stirred for 1 h. The reaction mixture was concentrated and dissolved in THF (1 mL). To the resulting solution was added an ethereal solution of diazomethane and the mixture was stirred for 1 h. After concentration, the crude material was purified by silica gel chromatography (gradient elution 9:1 hexanes:EtOAc to EtOAc) to give the diazoketone: mass spectrum m/z 264 [(M+H)$^+$; calcd for C$_{15}$H$_{10}$N$_3$O$_2$: 264].

A solution of the above diazoketone (20 mg, 0.07 mmol), silver benzoate (15 mg, 0.07 mmol) and triethylamine (0.15 mL) in MeOH (3 mL) was stirred at room temperature for 1 h. The reaction mixture was partitioned between EtOAc and aqueous NaHCO$_3$. The organic layers was dried over Na$_2$SO$_4$, filtered, concentrated and purified by silica gel chromatography (gradient elution 4:1 to 1:1 hexanes:EtOAc) to give methyl ester (S): $^1$H NMR (300 MHz, CDCl$_3$) δ7.59 (d, 1 H); 7.40 (m, 4 H), 7.05 (d, 2 H); 6.91 (d, 1 H); 3.74 (s, 3 H); 3.60 (s, 2 H) ppm.

Methyl ester (S) (10 mg, 0.04 mmol) was suspended in NaOH (1M, 1 ml) and was heated to 120° C. Methanol was added until the compound dissolved. The reaction mixture was immediately cooled, concentrated and purified by reverse-phase HPLC to give the corresponding acid (U).

To a solution of acid (U) (4 mg, 0.02 mmol) in DMF (0.3 mL) was added EDC (3.1 mg, 0.02 mmol), HOAt (2.2 mg, 0.02 mmol) and methanesulfonic acid (3,4-diaminophenyl)-amide (J) (3.2 mg, 0.02 mmol). The reaction mixture was stirred at room temperature for 3 h followed by quenching with aqueous NaHCO$_3$ and EtOAc. The layers were separated and the organic was washed twice with water, dried over Na$_2$SO$_4$, filtered and concentrated.

The crude product was dissolved in acetic acid (0.5 mL) and heated to 130° C. for 15 min. The reaction mixture was cooled, concentrated and partitioned between aqueous NaHCO$_3$ and EtOAc and the organic layer was dried over Na$_2$SO$_4$, filtered and concentrated. The crude oil was purified by reverse phase HPLC to give Example 53: mass spectrum m/z 419 [(M+H)$^+$; calcd for C$_{22}$H$_{19}$N$_4$O$_3$S: 419].

Pyridyl Center Ring Examples

Scheme 9

Compounds of this invention can be prepared by the following general procedure, scheme 9:

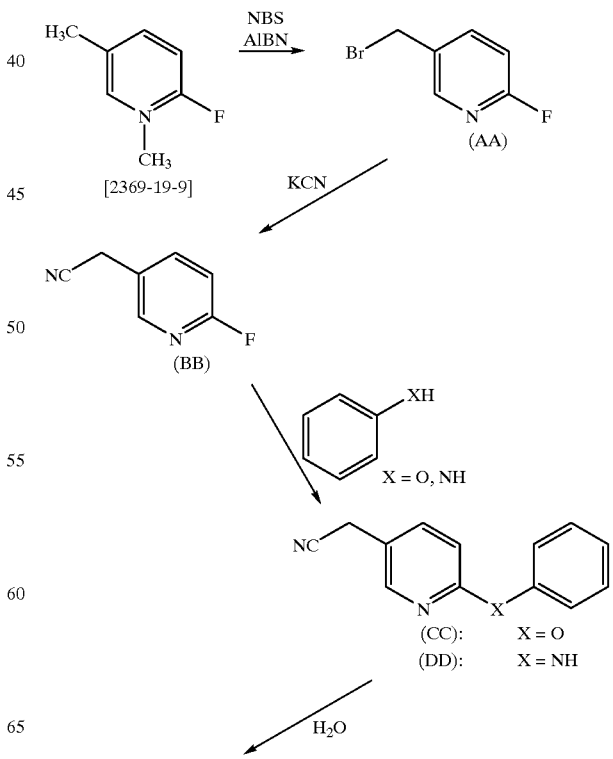

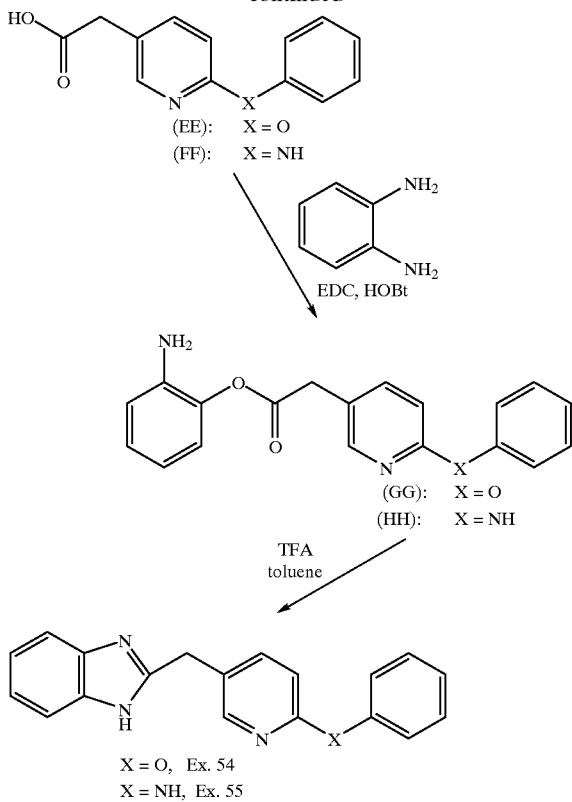

X = O, Ex. 54
X = NH, Ex. 55

Compound (AA):
5-(Bromomethyl)-2-fluoropyridine

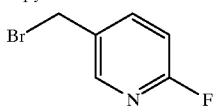

5-Methyl-2-fluoropyridine ([2369-19-9], 2.10 g, 18.90 mmol) and was dissolved in carbon tetrachloride (25 mL) and was treated with 2,2'-azobisisobutyronitrile (100 mg, 0.6 mmol) and N-bromosuccinimide (3.38 g, 19.00 mmol) in single portions. The reaction was stirred for 30 minutes at 80° C. under argon. The volatiles were removed under reduced pressure and the resulting residue was purified by flash column chromatography (silica; 10% to 25% ethyl acetate in hexane) to give 2.25 g of compound AA as a colorless oil (63%).
MS (EI): M/Z=189.9, 191.9.

Compound (BB):
(6-Fluoro-3-pyridinyl)acetonitrile

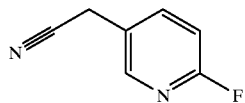

5-(Bromomethyl)-2-fluoropyridine (2.25 g, 11.84 mmol) was dissolved in methylsulfoxide (25 mL) and was treated with potassium cyanide (3.38 g, 19.00 mmol) in a single portion. The reaction aged 18 h at ambient temperature, was diluted with ethyl acetate and washed with saturated sodium bicarbonate, water and brine. The organics were dried over sodium sulfate, filtered and the volatiles removed under reduced pressure. The resulting residue was purified by flash column chromatography (silica; 20% to 50% ethyl acetate in hexane) to give 0.85 g of compound BB as a yellow oil (53%).
MS (EI) M/Z=137.0.

Compound (EE):
(6-Phenoxy-3-pyridinyl)acetic acid

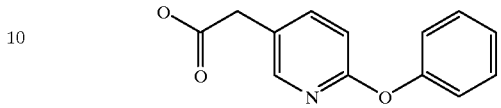

(6-Fluoro-3-pyridinyl)acetonitrile (60 mg, 0.44 mmol) and phenol (110 mg, 1.17 mmol) were dissolved in dimethylformamide (250 μL) and heated to 180° C. in a sealed tube for 18 h. The volatiles were removed in vacuo and the resulting residue (compound CC) was suspended in water (2 mL), treated with acetic acid (1 mL) and concentrated hydrochloric acid (1 mL) and heated to 110° C. in a sealed tube for 2 h. The volatiles were removed in vacuo leaving 111 mg of a brown oil which was used in the following step (see scheme 5) without purification.
MS (EI) M/Z=230.9.

Compound (FF):
(6-Anilino-3-pyridinyl)acetic acid

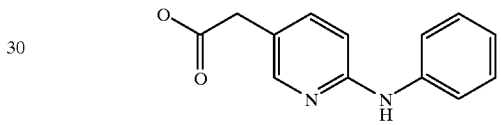

(6-Fluoro-3-pyridinyl)acetonitrile (93 mg, 0.68 mmol) and aniline (200 μL, 2.25 mmol) were dissolved in dimethylformamide (250 μL) and were heated to 180° C. in a sealed tube for 18 h. The volatiles were removed in vacuo and the resulting residue (compound DD) was suspended in water (2 mL), treated with acetic acid (1 mL), concentrated hydrochloric acid (1 mL) and heated to 110° C. in a sealed tube for 2 h. The volatiles were removed in vacuo affording 200 mg of a brown oil which was used in the next step (see scheme 5) without purification.
MS (EI) M/Z=229.0.

Example 54

2-[(6-Phenoxy-3-pyridinyl)methyl]-1H-benzimidazole (Ex. 54)

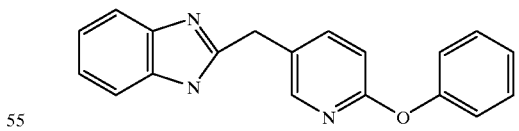

(6-Phenoxy-3-pyridinyl)acetic acid (101 mg, 0.44 mmol) was dissolved in dimethylformamide (1 mL) and was treated with 1-hydroxybenzotriazole (67 mg, 0.44 mmol), 1-ethyl-3-[3-(dimethylamino)propyl]-carbodiimide (84 mg, 0.44 mmol) and 1,2-phenylenediamine ([95-54-5])(48 mg, 0.44 mmol). The reaction aged 18 h was diluted with ethyl acetate and washed with saturated sodium bicarbonate, water and brine. The organics were dried over sodium sulfate, filtered and the volatiles removed under reduced pressure affording a yellow oil (compound GG). This material was dissolved in toluene (2 mL), treated with trifluoroacetic acid (1 mL), and heated to 100° C. for 1 h. The volatiles were then removed in vacuo and the resulting brown residue was purified by preparatory HPLC to give 7 mg of Example 54 as the trifluoroacetic acid salt (7%).

MS (EI) M/Z=302.0.

Example 55

5-(1H-Benzimidazol-2-ylmethyl)-N-phenyl-2-pyridinamine

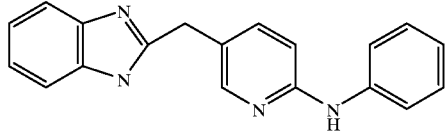

(Ex. 55)

(6-Anilino-3-pyridinyl)acetic acid (87 mg, 0.38 mmol) was dissolved in dimethylformamide and was treated with 1-hydroxybenzotriazole (58 mg, 0.38 mmol), 1-ethyl-3-[3-(dimethylamino)propyl]-carbodiimide (73 mg, 0.38 mmol) and 1,2-phenylenediamine (41 mg, 0.38 mmol). The reaction aged 18 h was diluted with ethyl acetate and washed with sat. saturated sodium bicarbonate, water and brine. The organics were dried over sodium sulfate, filtered and the volatiles removed under reduced pressure affording a yellow oil which was purified by flash column chromatography (silica; 95 $CH_2Cl_2$: 5 $CH_3OH$:0.5 $NH_4OH$) to give 7 mg of compound HH (MS (EI) M/Z=319.0). This material was dissolved in toluene (2 mL), treated with trifluoroacetic acid (1 mL) and heated to 100° C. for 1 h. The volatiles were then removed in vacuo leaving 12 mg of Example 55 as a brown oil (6%).

MS (EI) M/Z=301.0.

What is claimed is:

1. A compound having the formula:

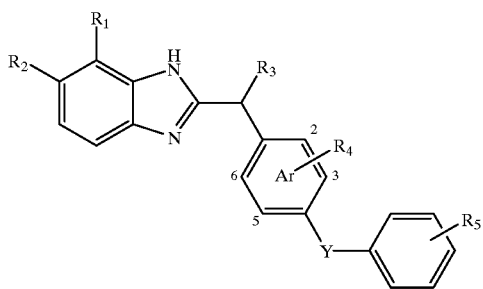

(I)

or pharmaceutically acceptable salts thereof, wherein $R_1$, $R_2$, $R_4$, and $R_5$ are independently H, chloro, fluoro, hydroxy, methoxy, trifluoromethyl, trifluoromethoxy, amino, cyano, nitro, $C_{1-7}$alkyl, aryl, amino$C_{1-4}$alkyl, $C_{1-4}$alkyl-carbonylamino, oxo-hydroxy-dibenzopyranyl-carboxyphenyl-thioueido, $R_6SO_2NH$—, $R_6SO_2N(CH_3)$—, $R_6SO_2NHCH_2$—, or oxo-hydroxy-dibenzopyranyl-carboxyphenyl-substituted carbonylamino-$C_{1-4}$alkyl-carbonylamino;

$R_3$ is H, OH, $NH_2$, alkyl amine, arylamine, or a carbonyl oxygen;

$R_6$ is $C_{1-6}$alkyl, $C_{1-6}$alkenyl, phenyl$C_{1-3}$alkenyl, phenyl, naphthyl, or heterocyclic group, optionally substituted with 1–6 substituents, each substituent independently being halogen, $C_{1-4}$alkyl, $C_{1-4}$alkoxy, halo$C_{1-4}$alkoxy, amino, $C_{1-4}$alkylamino, di$C_{1-4}$alkylamino, $C_{1-4}$alkylcarbonylamino, phthalimidyl, phenylsulfonyl, or oxo-hydroxy-dibenzopyranyl-carboxyphenyl-thioueido;

Y is O, NH, $(CH_2)_nCO(CH_2)_n$, $(CH_2)_nCHR_3(CH_2)_n$, n is independently 0, 1, 2, 3, 4, or 5; and the central ring Ar is substituted with 0–3 nitrogen heteroatoms at any of positions 2, 3, 5, or 6.

2. The compound according to claim 1, or a pharmaceutically acceptable salt thereof, wherein:

$R_1$, $R_2$, $R_4$, and $R_5$ are independently H, chloro, fluoro, hydroxy, methoxy, trifluoromethyl, trifluoromethoxy, amino, cyano, nitro, $C_{1-7}$alkyl, aryl, amino$C_{1-4}$alkyl, $C_{1-4}$alkyl-carbonylamino, oxo-hydroxy-dibenzopyranyl-carboxyphenyl-thioueido, $R_6SO_2NH$—, $R_6SO_2N(CH_3)$—, $R_6SO_2NHCH_2$—, or oxo-hydroxy-dibenzopyranyl-carboxyphenyl-substituted carbonylamino-$C_{1-4}$alkyl-carbonylamino;

$R_3$ is H, OH, $NH_2$, alkyl amine, arylamine, or a carbonyl oxygen;

$R_6$ is $C_{1-6}$alkyl, $C_{1-6}$alkenyl, phenyl$C_{1-3}$alkenyl, phenyl, naphthyl, or heterocyclic group, optionally substituted with 1–6 substituents, each substituent independently being halogen, $C_{1-4}$alkyl, $C_{1-4}$alkoxy, halo$C_{1-4}$alkoxy, amino, $C_{1-4}$alkylamino, di$C_{1-4}$alkylamino, phthalimidyl, $C_{1-4}$alkylcarbonylamino, phenylsulfonyl, or oxo-hydroxy-dibenzopyranyl-carboxyphenyl-thioueido;

Y is O; and the central ring Ar is substituted with 0–3 nitrogen heteroatoms at any of positions 2, 3, 5, or 6.

3. The compound according to claim 1, or a pharmaceutically acceptable salt thereof, wherein:

$R_1$, $R_2$, and $R_4$ are independently H, chloro, fluoro, hydroxy, methoxy, trifluoromethyl, trifluoromethoxy, amino, cyano, nitro, $C_{1-7}$alkyl, aryl, amino$C_{1-4}$alkyl, $C_{1-4}$alkyl-carbonylamino, oxo-hydroxy-dibenzopyranyl-carboxyphenyl-thioueido, $R_6SO_2NH$—, $R_6SO_2N(CH_3)$—, $R_6SO_2NHCH_2$—, or oxo-hydroxy-dibenzopyranyl-carboxyphenyl-substituted carbonylamino-$C_{1-4}$alkyl-carbonylamino;

$R_5$ is H;

$R_3$ is H, OH, $NH_2$, alkyl amine, arylamine, or a carbonyl oxygen;

$R_6$ is $C_{1-6}$alkyl, $C_{1-6}$alkenyl, phenyl$C_{1-3}$alkenyl, phenyl, naphthyl, or heterocyclic group, optionally substituted with 1–6 substituents, each substituent independently being halogen, $C_{1-4}$alkyl, $C_{1-4}$alkoxy, halo$C_{1-4}$alkoxy, amino, $C_{1-4}$alkylamino, di$C_{1-4}$alkylamino, phthalimidyl, $C_{1-4}$alkylcarbonylamino, phenylsulfonyl, or oxo-hydroxy-dibenzopyranyl-carboxyphenyl-thioueido;

Y is O, NH, $(CH_2)_nCO(CH_2)_n$, $(CH_2)_nCHR_3(CH_2)_n$, n is independently 0, 1, 2, 3, 4, or 5; and the central ring Ar is substituted with 0–3 nitrogen heteroatoms at any of positions 2, 3, 5, or 6.

4. The compound according to claim 1, or a pharmaceutically acceptable salt thereof, wherein:

$R_1$, $R_2$, and $R_4$ are independently H, chloro, fluoro, hydroxy, methoxy, trifluoromethyl, trifluoromethoxy, amino, cyano, nitro, $C_{1-7}$alkyl, aryl, amino$C_{1-4}$alkyl, $C_{1-4}$alkyl-carbonylamino, oxo-hydroxy-dibenzopyranyl-carboxyphenyl-thioueido, $R_6SO_2NH$—, $R_6SO_2N(CH_3)$—, $R_6SO_2NHCH_2$—, or oxo-hydroxy-dibenzopyranyl-carboxyphenyl-substituted carbonylamino-$C_{1-4}$alkyl-carbonylamino;

$R_5$ is H;

$R_3$ is H, OH, $NH_2$, alkyl amine, arylamine, or a carbonyl oxygen;

$R_6$ is $C_{1-6}$alkyl, $C_{1-6}$alkenyl, phenyl$C_{1-3}$alkenyl, phenyl, naphthyl, or heterocyclic group, optionally substituted with 1–6 substituents, each substituent independently being halogen, $C_{1-4}$alkyl, $C_{1-4}$alkoxy, halo$C_{1-4}$alkoxy, amino, $C_{1-4}$alkylamino, di$C_{1-4}$alkylamino, $C_{1-4}$alkylcarbonylamino, phthalimidyl, phenylsulfonyl, or oxo-hydroxy-dibenzopyranyl-carboxyphenyl-thioueido;

Y is O; and the central ring Ar is substituted with 0–3 nitrogen heteroatoms at any of positions 2, 3, 5, or 6.

5. The compound according to claim 1, wherein said compound is

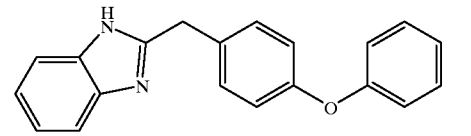

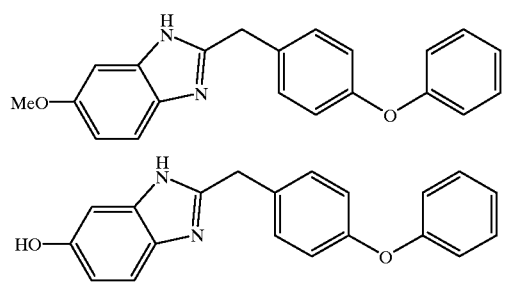

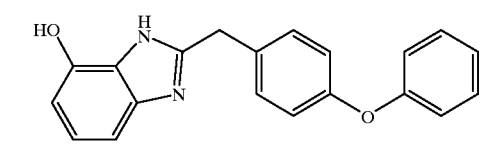

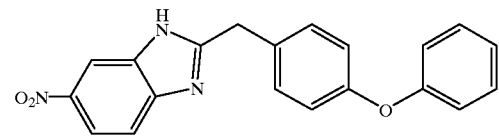

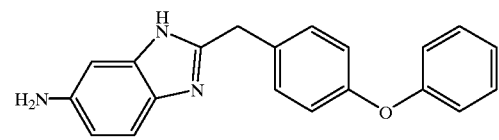

or a pharmaceutically acceptable salt thereof.

6. The compound according to claim 1 wherein said compound is

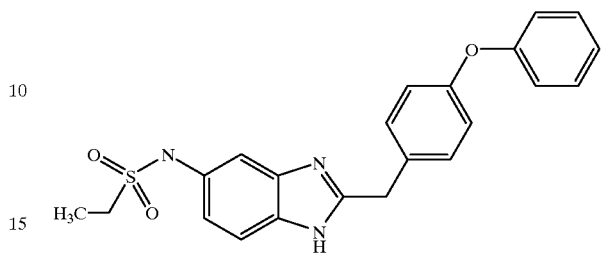

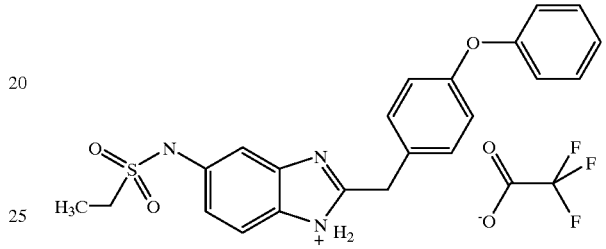

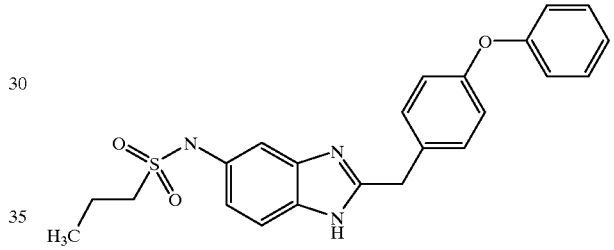

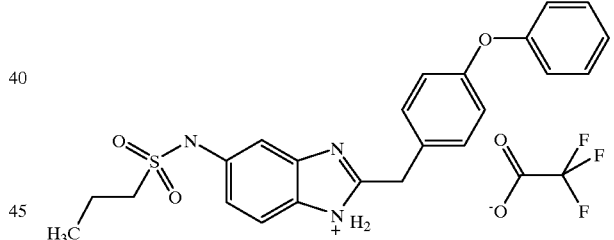

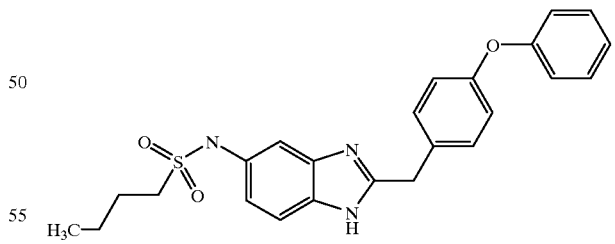

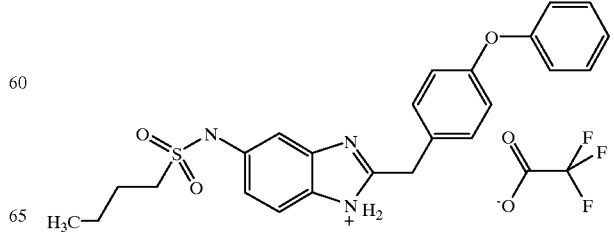

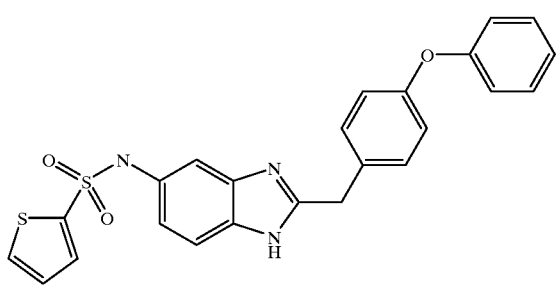

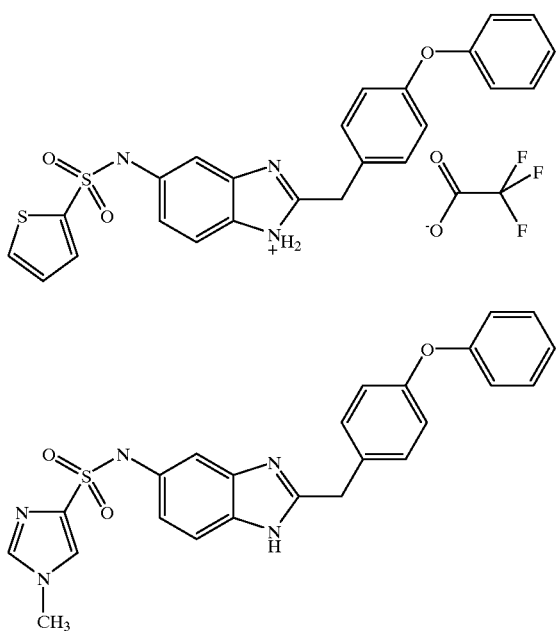

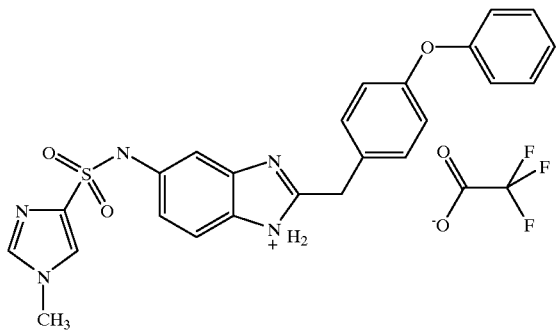

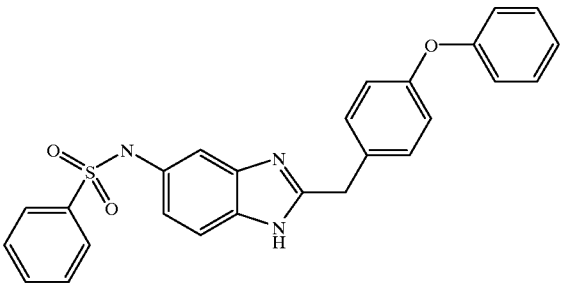

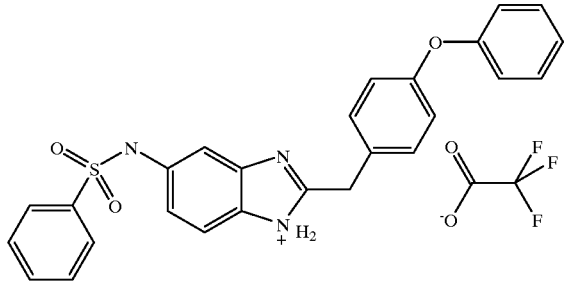

or a pharmaceutically acceptable salt thereof.

7. The compound according to claim 1 wherein said compound is 2-(4-Phenoxy-benzyl)-1H-benzimidazole;
6-Methoxy-2-(4-phenoxy-benzyl)-1H-benzimidazole;
2-(4-Phenoxy-benzyl)-3H-benzimidazol-5-ol;
2-(4-Phenoxy-benzyl)-3H-benzimidazol-4-ol;
6-Nitro-2-(4-phenoxy-benzyl)-1H-benzimidazole;
2-(4-Phenoxy-benzyl)-3H-benzimidazol-5-ylamine;
N-[2-(4-Phenoxy-benzyl)-3H-benzimidazol-5-yl]-methanesulfonamide;
Ethanesulfonic acid[2-(4-phenoxy-benzyl)-3H-benzimidazol-5-yl]amide;
Propane-1-sulfonic acid[2-(4-phenoxy-benzyl)-3H-benzimidazol-5-yl]amide;
Butane-1-sulfonic acid[2-(4-phenoxy-benzyl)-3H-benzimidazol-5-yl]amide;
Thiopene-2-sulfonic acid[2-(4-phenoxy-benzyl)-3H-benzimidazol-5-yl]amide;
1-Methyl-1H-imidazole-4-sulfonic acid[2-(4-phenoxy-benzyl)-3H-benzimidazol-5-yl]amide;
N-[2-(4-phenoxy-benzyl)-3H-benzimidazol-5-yl]benzenesulfonamide;

or a pharmaceutically acceptable salt thereof.

8. The compound according to claim 1, wherein said compound is

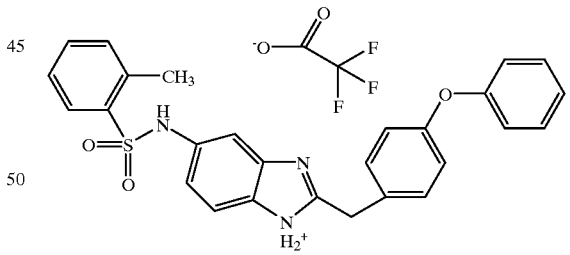

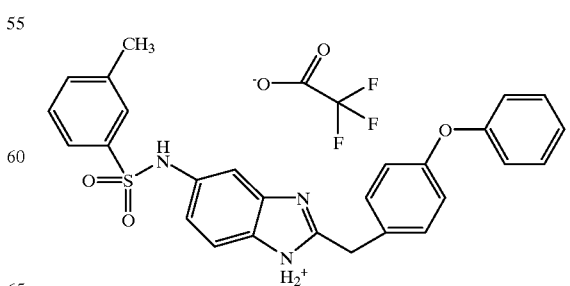

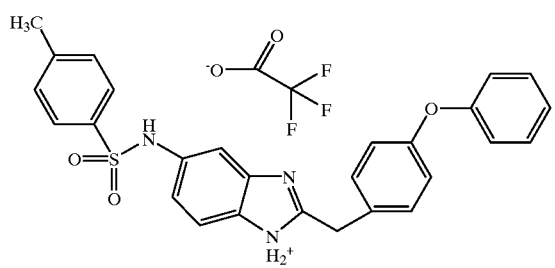
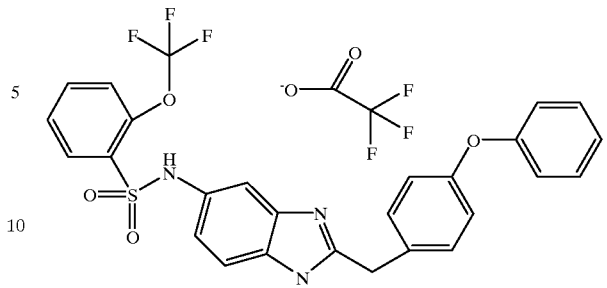
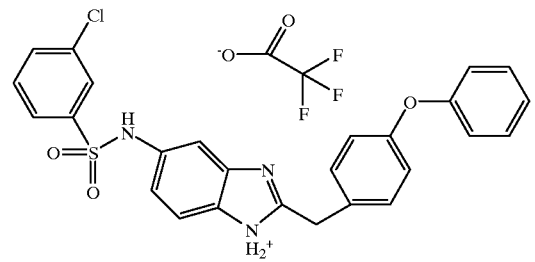
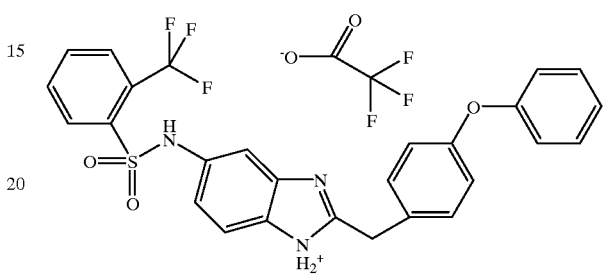
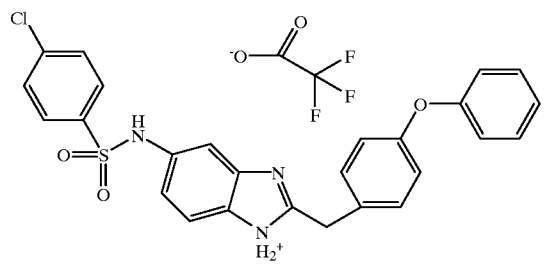
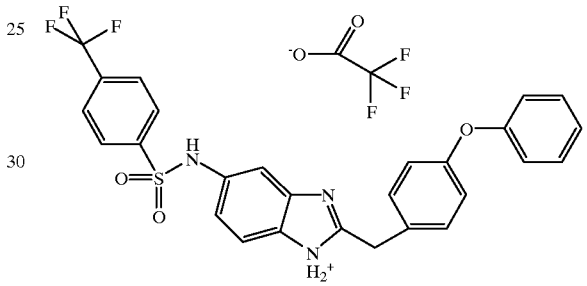
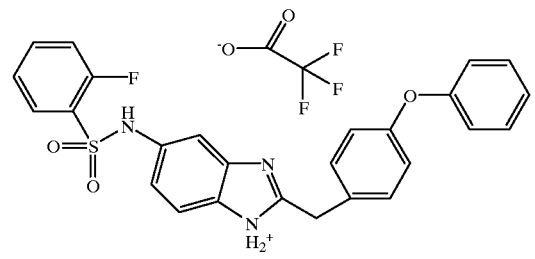
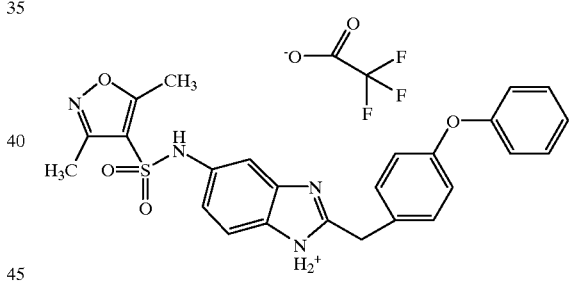
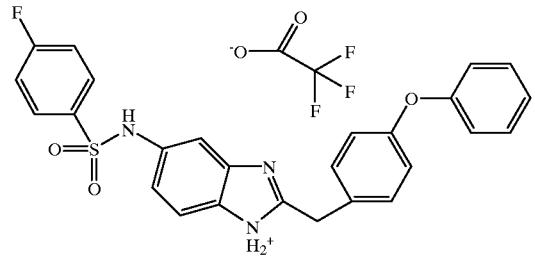
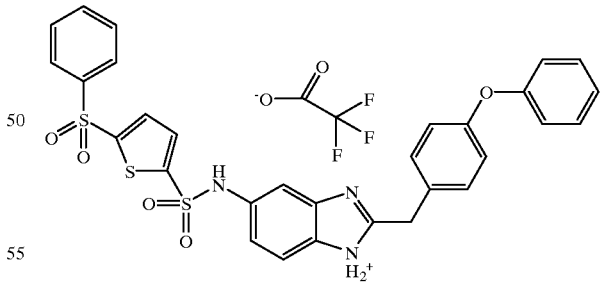
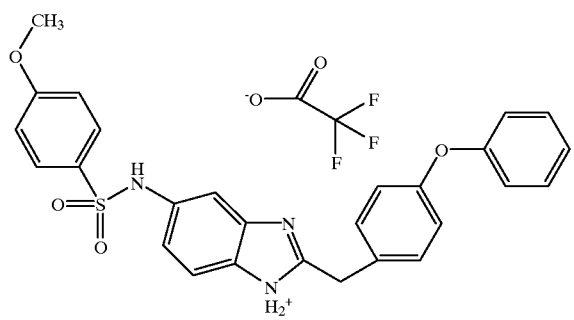
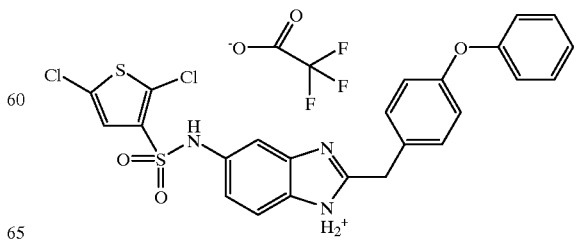

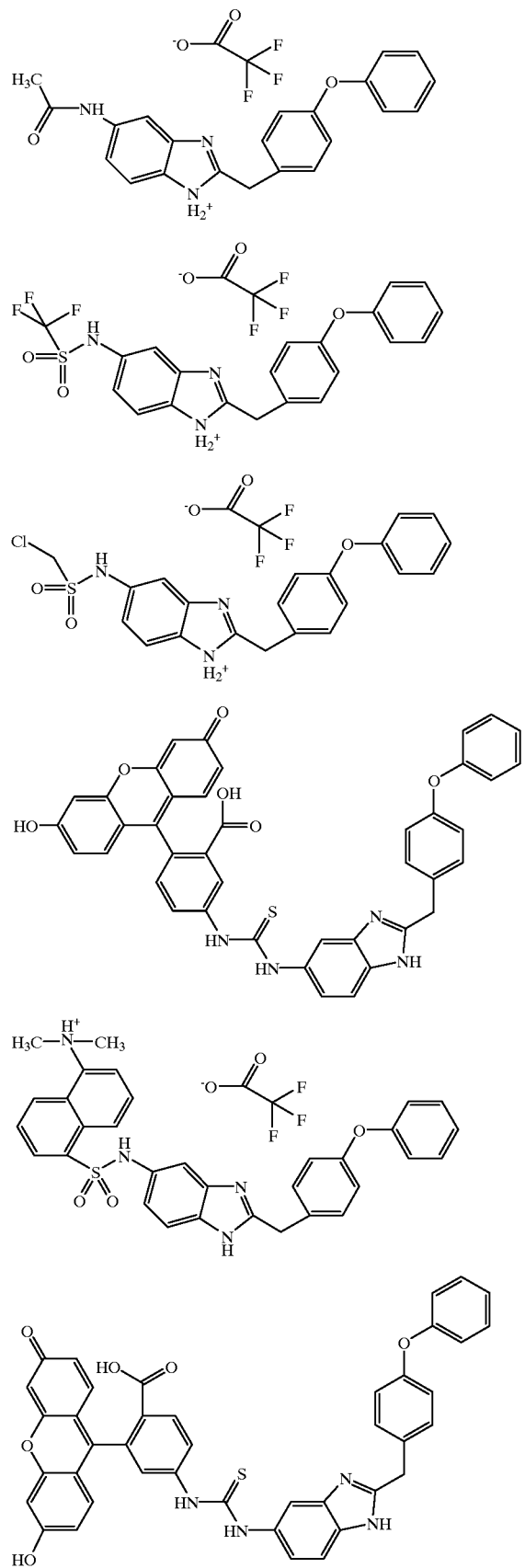
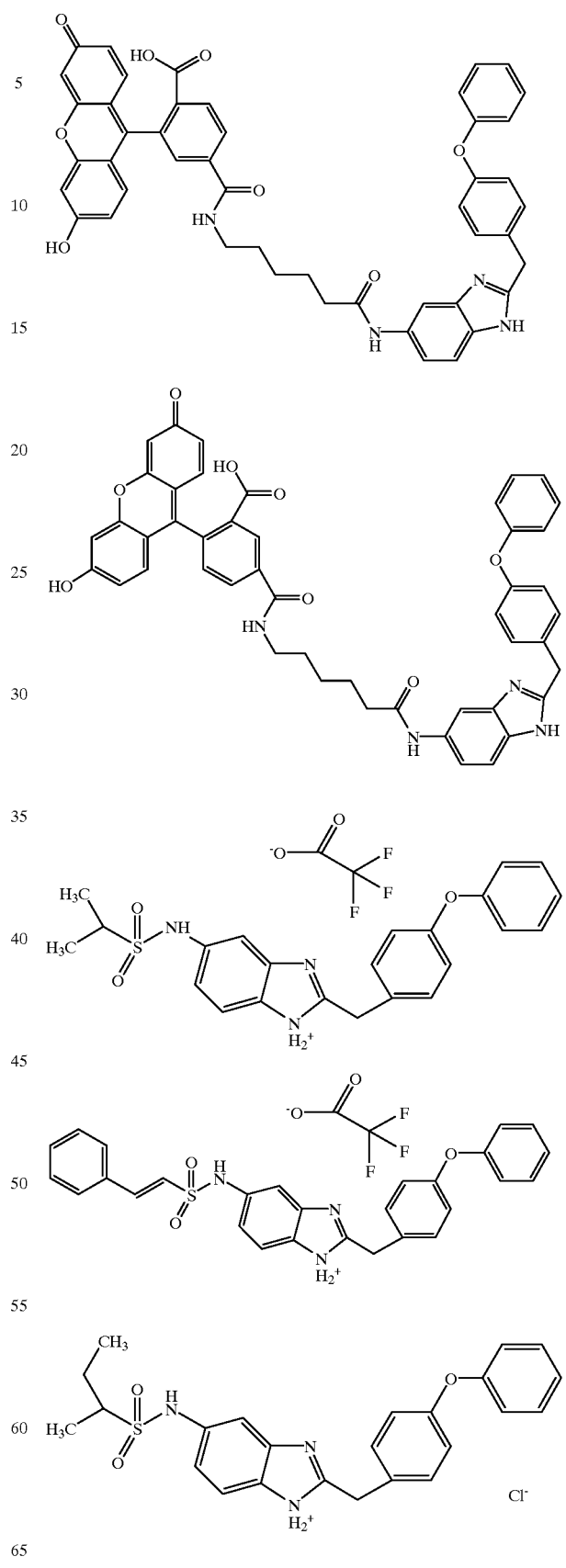

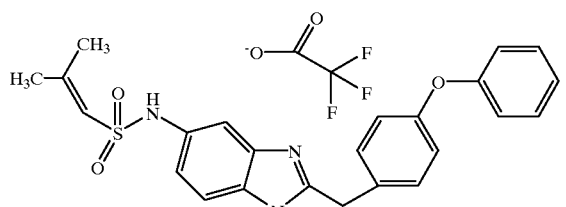
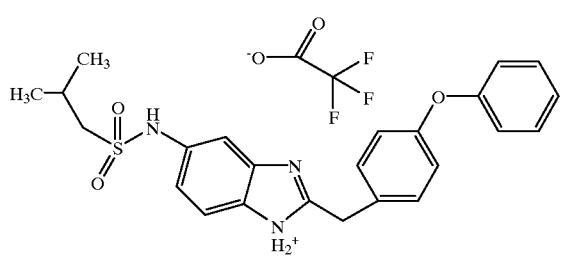
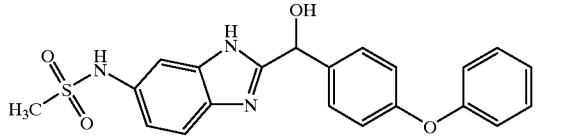
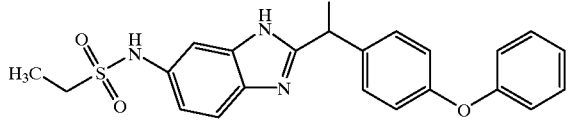
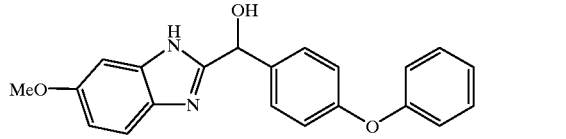
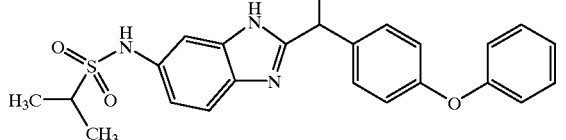
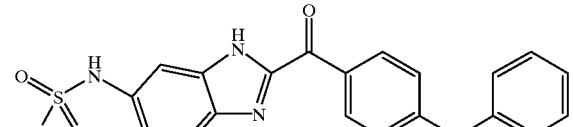
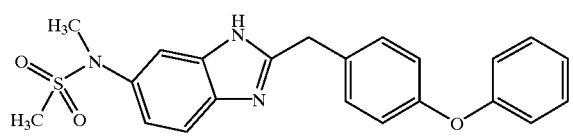
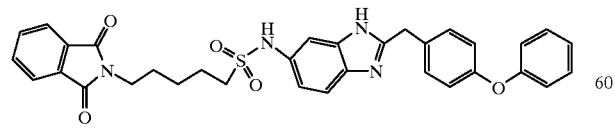
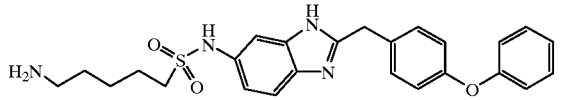
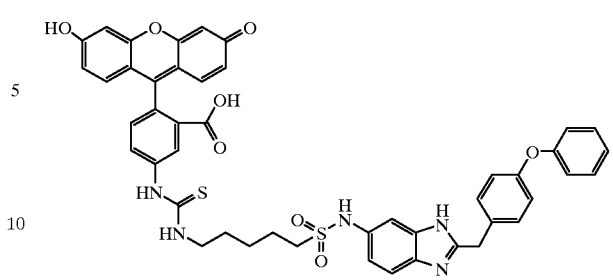
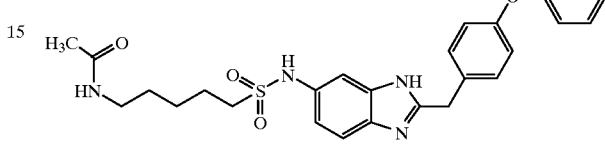
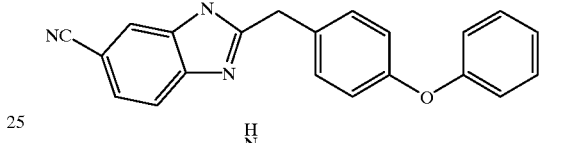
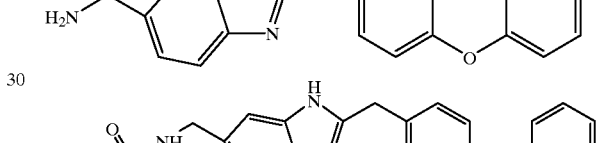
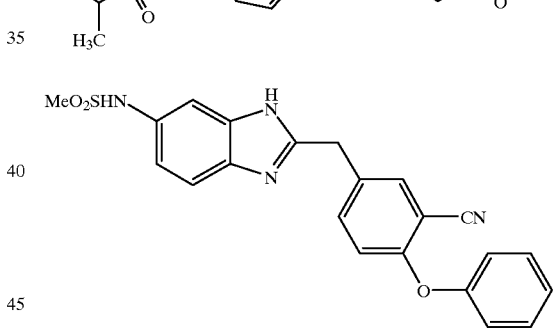
or a pharmaceutically acceptable salt thereof.
9. The compound according to claim 1, wherein said compound is
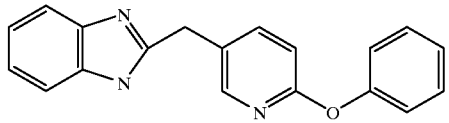
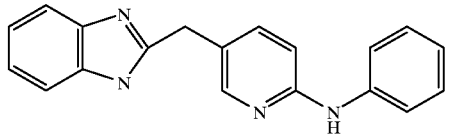
or a pharmaceutically acceptable salt thereof.
10. A pharmaceutical composition comprising an inert carrier and an effective amount of a compound according to claim 1.

11. The pharmaceutical composition according to claim 10 useful for the treatment of pain.

12. The pharmaceutical composition according to claim 10 useful for the treatment of pain, depression, schizophrenia, Parkinson's disease, or stroke.

13. A method of treating pain comprising a step of administering to one in need of such treatment an effective amount of a compound according to claim 1.

* * * * *